US010131701B2

(12) United States Patent
Rozanov et al.

(10) Patent No.: US 10,131,701 B2
(45) Date of Patent: Nov. 20, 2018

(54) HUMAN LEUCINE ZIPPER/TRAIL RECOMBINANT POLYPEPTIDES

(71) Applicants: OREGON HEALTH & SCIENCE UNIVERSITY, Portland, OR (US); SANFORD BURNHAM PREBYS MEDICAL DISCOVERY INSTITUTE, La Jolla, CA (US)

(72) Inventors: Dmitri Rozanov, Lake Oswego, OR (US); Alexander Aleshin, La Jolla, CA (US)

(73) Assignees: Oregon Health & Science University, Portland, OR (US); Sanford Burnham Prebys Medical Discovery Institute, La Jolla, CA (US)

( * ) Notice: Subject to any disclaimer, the term of this patent is extended or adjusted under 35 U.S.C. 154(b) by 0 days.

(21) Appl. No.: 15/081,300

(22) Filed: Mar. 25, 2016

(65) Prior Publication Data
US 2016/0280761 A1 Sep. 29, 2016

Related U.S. Application Data

(60) Provisional application No. 62/139,155, filed on Mar. 27, 2015.

(51) Int. Cl.
| | |
|---|---|
| *C07K 14/705* | (2006.01) |
| *A61K 38/16* | (2006.01) |
| *C07K 14/52* | (2006.01) |
| *C07K 14/715* | (2006.01) |
| *C07K 14/47* | (2006.01) |
| *A61K 38/00* | (2006.01) |

(52) U.S. Cl.
CPC .......... *C07K 14/52* (2013.01); *C07K 14/4705* (2013.01); *C07K 14/715* (2013.01); *A61K 38/00* (2013.01); *C07K 2319/73* (2013.01)

(58) Field of Classification Search
CPC .... A61K 38/00; C07K 2319/73; C07K 14/52; C07K 14/715; C07K 14/4705
See application file for complete search history.

(56) References Cited

U.S. PATENT DOCUMENTS

2014/0206843 A1 7/2014 Zhou et al.

FOREIGN PATENT DOCUMENTS

CN 102898526 A * 1/2013 ....... C07K 14/70575

OTHER PUBLICATIONS

Machine translation of CN 102898526 A, pp. 1-13, accessed Oct. 1, 2017.*

Aroui, et al., "Conjugation of doxorubicin to cell penetrating peptides sensitizes human breast MDA-MB 231 cancer cells to endogenous TRAIL-induced apoptosis," Apoptosis, vol. 14, 2009, pp. 1352-1365.
Ashkenazi, et al., "Safety and antitumor activity of recombinant soluble Apo2 ligand," J. Clin. Invest., vol. 104, No. 2, 1999, pp. 155-162.
Ashkenazi, et al., "Targeting the extrinsic apoptosis pathway in cancer," Cytokine Growth Factor Rev., vol. 19, 2008, pp. 325-331.
Ashkenazi, et al., "Targeting death and decoy receptors of the tumour-necrosis factor superfamily," Nat. Rev. Cancer, vol. 2, 2002, pp. 420-430.
Bodmer, et al., "Cysteine 230 Is Essential for the Structure and Activity of the Cytotoxic Ligand TRAIL," J. Biol. Chem., vol. 275, 2000, pp. 20632-20637.
Cheng, et al., "BCL-2, BCL-XL Sequester BH3 Domain-Only Molecules Preventing BAX- and BAK-Mediated Mitochondrial Apoptosis," Mol. Cell., vol. 8, No. 2, 2001, pp. 705-711.
Elmore, "Apoptosis: A Review of Programmed Cell Death," Toxicol. Pathol., vol. 35, No. 4, 2007, pp. 495-516.
Falschlehner, at al., "TRAIL signalling: Decisions between life and death," Int. J. Biochem. Cell Biol., vol. 39, 2007, pp. 1462-1475.
Fong, et al., "Predicting specificity in bZIP coiled-coil protein interactions," Genome Biol., vol. 5, No. 2, 2004, 10 pages.
Fuchs and Steller, "Programmed Cell Death in Animal Development and Disease," Cell, vol. 147, No. 4, 2011, pp. 742-758.
Fulda and Debatin, "Extrinsic versus intrinsic apoptosis pathways in anticancer chemotherapy," Oncogene, vol. 25, No. 34, 2006, pp. 4798-4811.
Harbury, et al., "A switch between two-, three-, and four-stranded coiled coils in GCN4 leucine zipper mutants," Science, vol. 262, No. 5138, 1993, pp. 1401-1407.
Hymowitz, et al., "Triggering cell death: the crystal structure of Apo2L/TRAIL in a complex with death receptor 5," Mol. Cell., vol. 4, No. 4, 1999, pp. 563-571.
Johnstone, et al., "The TRAIL apoptotic pathway in cancer onset, progression and therapy," Nat. Rev. Cancer, vol. 8, No. 10, 2008, pp. 782-799.
Kandasamy, et al., "Involvement of proapoptotic molecules Bax and Bak in tumor necrosis factor-related apoptosis-inducing ligand (TRAIL)-induced mitochondrial disruption and apoptosis: differential regulation of cytochrome c and Smac/DIABLO release," Cancer Res., vol. 63, No. 7, 2003, pp. 1712-1721.
Lacroix, et al., "Elucidating the folding problem of a-helices: local motifs, long-range electrostatics, ionic-strength dependence and prediction of NMR parameters," J. Mol. Biol., vol. 284, No. 1, 1998, pp. 173-191.
Lemke, et al., "Getting TRAIL back on track for cancer therapy," Cell Death Differ., vol. 21, No. 9, 2014, pp. 1350-1364.

(Continued)

*Primary Examiner* — Julie Ha
*Assistant Examiner* — Li N Komatsu
(74) *Attorney, Agent, or Firm* — Lee & Hayes PC; C. Rachal Winger

(57) ABSTRACT

Disclosed are recombinant polypeptides that include human TRAIL sequences as well as human leucine zipper motifs as well as polynucleotides that encode the recombinant polypeptides, expression vectors that comprise the polynucleotides, pharmaceutical compositions comprising the polypeptides, and methods of using the pharmaceutical compositions for the treatment of cancer. Further disclosed are TRAIL sequences with stabilizing mutations and methods of expressing the disclosed polypeptides in *E. coli*.

8 Claims, 5 Drawing Sheets
Specification includes a Sequence Listing.

(56) References Cited

OTHER PUBLICATIONS

Park, et al., "Beta-sitosterol sensitizes MDA-MB-231 cells to TRAIL-induced apoptosis," Acta Pharmacol. Sin., vol. 29, No. 3, 2008, pp. 341-348.
Pitti, et al., "Induction of apoptosis by Apo-2 ligand, a new member of the tumor necrosis factor cytokine family," J. Biol. Chem., vol. 271, No. 22, 1996, pp. 12687-12690.
Rosanov, et al., "A Humanized Leucine Zipper-TRAIL Hybrid Induces Apoptosis of Tumors both In Vitro and In Vivo," PLOS One, vol. 10, No. 4, 2015, e0122980, 13 pages.
Rozanov, et al., "Engineering a leucine zipper-TRAIL homotrimer with improved cytotoxicity in tumor cells," Mol. Cancer Ther., vol. 8, No. 6, 2009, pp. 1515-1525.
Song, et al., "TRAIL triggers apoptosis in human malignant glioma cells through extrinsic and intrinsic pathways," Brain Pathol., vol. 13, No. 4, 2003, pp. 539-553.
Tait and Green, "Mitochondria and cell death: outer membrane permeabilization and beyond," Nat. Rev. Mol. Cell Biol., vol. 11, No. 9, 2010, pp. 621-632.
Walczak, et al., "Tumoricidal activity of tumor necrosis factor-related apoptosis-inducing ligand in vivo," Nat. Med., vol. 5, No. 2, 1999, pp. 157-163.
Wang, "The promise of cancer therapeutics targeting the TNF-related apoptosis-inducing ligand and TRAIL receptor pathway," Oncogene, vol. 27, No. 48, 2008, pp. 6207-6215.
Wiley, et al., "Identification and characterization of a new member of the TNF family that induces apoptosis," Immunity, vol. 3, No. 6, 1995, pp. 673-682.
Zhang and Zhang, "TRAIL Resistance of Breast Cancer Cells Is Associated with Constitutive Endocytosis of Death Receptors 4 and 5," Mol. Cancer Res., vol. 6, No. 12, 2008, pp. 1861-1871.
Bjelic, et al., "Structural Basis for the Oligomerization-State Switch from a Dimer to a Trimer of an Engineered Cortexillin-1 Coiled-Coil Variant," PLoS One, vol. 8, No. 5, 2013, 7 pages.
Shaw, et al., "Inducible release of TRAIL fusion proteins from a proapoptotic form for tumor therapy," Cancer Res., vol. 64, No. 9, 2004, pp. 3236-3242.
Search Report and Written Opinion dated Jul. 25, 2016 in International Patent Application No. PCT/US16/24227.

* cited by examiner

HUMAN LEUCINE ZIPPER/TRAIL RECOMBINANT POLYPEPTIDES

CROSS-REFERENCE TO RELATED APPLICATION

This application claims priority to 62/139,155 filed on Mar. 27, 2015, which is incorporated herein by reference in its entirety as if fully set forth herein.

ACKNOWLEDGEMENT OF GOVERNMENT SUPPORT

This invention was made with the support of the United States government under the terms of grant number W81XWH-09-1-0601, awarded by the Department of Defense.

FIELD

Generally, the field is recombinant polypeptides. More specifically, the field is therapeutic humanized recombinant polypeptides for use in the treatment of cancer.

REFERENCE TO SEQUENCE LISTING

A computer readable text file, entitled "DN10G0188.txt (Sequence Listing.txt)" created on or about Jun. 27, 2017, with a file size of about 49 KB, contains the sequence listing for this application and is hereby incorporated by reference in its entirety.

BACKGROUND

Apoptosis is crucial for normal development and homeostasis in metazoans (Fuchs Y and Steller H, Cell 147, 742-758 (2011); incorporated by reference herein). Mammals and lower vertebrates have evolved a unique signaling mechanism, termed apoptosis that, under certain circumstances, programs individual cells to die (Elmore S, Toxicol Pathol 35, 495-516 (2007); incorporated by reference herein). Alternatively, induction of apoptosis is essential for the elimination of oncogenically transformed cells. Multiple cellular pathways triggering apoptosis are described. Over the years, the two main apoptotic pathways, the extrinsic and intrinsic pathways, have been studied in a great detail. The extrinsic pathway involves the interaction of ligands, including TNF, FasL, and TRAIL, with their respective receptors and the consequential activation of the downstream caspases and Bcl-2 family members (Fulda S and Debatin K M, Oncogene 25, 4798-4811 (2006) and Tait S W and Green D R, Nat Rev Mol Cell Biol 11, 621-632 (2010); both of which are incorporated by reference herein). The intrinsic pathway is triggered by internal signals (e.g., DNA damage) that are produced following cellular stress and involves the mitochondria. Initiation of either pathway results in the activation of chain-like caspases followed by proteolysis of cellular proteins and the degradation of chromosomal DNA.

TRAIL is able to trigger apoptosis in a variety of tumor cells but not in normal cells (Ashkenazi A et al, J Clin Invest 104, 155-162 (1999); Walczak H et al, Nat Med 5, 157-163 (1999); Pittim R M et al, J Biol Chem 271, 12687-12690 (1996); Wang S, Oncogene 27, 6207-6215 (2008); and Ashkenazi A, Cytokine Growth Factor Rev 19, 325-331 (2008); all of which are incorporated by reference herein). TRAIL is a type II membrane protein and, similar to TNF-α, TRAIL can be shed from the cell surface membrane to produce a soluble, biologically active form. Expression of TRAIL transcripts has been detected in many human tissues, mostly in the spleen, lung, and prostate (Wiley S R et al, Immunity 3, 673-682 (1995) and Ashkenazi A, Nat Rev Cancer 2, 420-430 (2002); both of which are incorporated by reference herein). TRAIL forms homotrimers with a stoichiometric zinc atom bound by the cysteine residue of each molecule in the trimeric ligand. Zn stabilizes the TRAIL homotrimer and is essential for its biological activity (Hymowitz S G et al, Mol Cell 4, 563-571 (1999) and Bodmer J L et al, J Biol Chem 275, 20632-20637 (2000); both of which are incorporated by reference herein).

TRAIL induces apoptosis by utilizing components of both the extrinsic and intrinsic cellular pathways (Song J H et al, Brain Pathol 13, 539-553 (2003) and Falschlehner C et al, Intl Biochem Cell Biol 39, 1462-1475 (2007); both of which are incorporated by reference herein). In the extrinsic pathway, apoptosis is initiated by the interaction of TRAIL with its respective death receptors, DR4 and DR5. These interactions lead to the receptor trimerization, to the clustering of the receptor's intracellular death domains (DD), and to the formation of the death-inducing signaling complex (DISC). DISC formation leads to the recruitment of an adaptor molecule, FADD, with the subsequent binding and activation of apical caspase-8 and apical caspase-10. Activated caspase-8 and -10 then cleave and activate the 'executioner' caspases-3 and other downstream caspases, followed by the cleavage of the death substrates and, eventually, cell death.

The TRAIL-induced intrinsic pathway involves the cleavage of the proapoptotic Bcl-2 family member Bid by active caspase-8. Truncated Bid is then translocated to the mitochondria where it promotes the release of cytochrome c and SMAC/DIABLO into the cytosol via interactions with the proapoptotic proteins Bax and Bak (Wei M C et al, Cancer Res 63, 1712-1721 (2003); incorporated by reference herein). By binding to the adaptor protein APAF-1, cytochrome c induces the formation of 'apoptosome', a structure that activates caspase-9. Proteolytically active caspase-9 in turn causes activation of the so called 'executioner' proteases (caspases-3, -6, and -7) in the presence of dATP, which leads to the cleavage of the death substrates. Antiapoptotic Bcl-2 family members Bcl-2 and Bcl-XL block cytochrome c release and, therefore, are negative regulators of the intrinsic apoptotic pathway (Cheng E H et al, Mol Cell 8, 705-711 (2001); incorporated by reference herein). TRAIL, by employing both the extrinsic and intrinsic apoptosis signaling pathways, amplifies the apoptotic signal initiated through its binding to the death receptors. The existence of two signaling apoptotic pathways mediated by TRAIL reveals the existence of two different cell types (Lemke J et al, Cell Death Differ 21, 1350-1364 (2014); incorporated by reference herein). In one cell type (type I), the apoptotic pathway is independent of the mitochondria and depends on the caspase-8 activation followed by the activation of effector caspases such as caspase-3. In the other cell type (type II), apoptosis is dependent on the amplification of the apoptotic signal via the mitochondrial (intrinsic) pathway. Overexpression of the anti-apoptotic Bcl-2 protein does not affect apoptosis in type I cells, but blocks apoptosis in type II cells.

SUMMARY

Disclosed are recombinant polypeptides that comprise a first sequence that is at least 90% identical to SEQ ID NO: 21 herein and a second sequence that comprises a human leucine zipper motif with 'a' and 'd' isoleucine substitutions.

The second sequence can be any such sequence including SEQ ID NOs: 1-19 herein. The recombinant polypeptide can further comprise a linker between the first sequence and the second sequence. The linker can be any linker of any length including linkers with the amino acid sequences: KGSG (SEQ ID NO: 37), GSG, SG, or RGSG (SEQ ID NO: 38). Examples of such polypeptides can comprise SEQ ID NO: 20.

In still further examples, the first sequence comprises one or more stabilizing mutations such as S133P, S156C, L169C, T127C, or H270C. Examples of sequences comprising such mutations include SEQ ID NOs: 22-28.

In still further examples, the polypeptide lacks a linker between the first and second sequence. Examples of such sequences include SEQ ID NOs: 29-35.

Also disclosed are polynucleotides that encode the recombinant polypeptide. Such polynucleotides can be provided in an expression vector. The expression vector comprises a promoter operably linked to the polynucleotide. The promoter can be any promoter including a constituitively active, inducible, conditional, or tissue specific promoter. The polynucleotide can be codon optimized for expression in yeast (such as *Pichia pastoris*) or *E. coli* expression systems.

Also disclosed are pharmaceutical compositions comprising an effective amount of the disclosed polypeptides (or polynucleotides) and a pharmaceutically acceptable carrier. These pharmaceutical compositions can be for use in the treatment of cancer.

Also disclosed are methods of treating cancer in a subject. Such methods comprise administering the disclosed pharmaceutical compositions to a subject.

Also disclosed are methods of expressing the disclosed polypeptides. Such methods involve transfecting an *E. coli* cell with the disclosed expression vector, provided that the expression vector comprises an inducible promoter. The transfected *E. coli* cell is used to inoculate a media. The media comprises zinc chloride. Then expression is induced. In some examples, the media comprises zinc chloride at a concentration of at least 50 μM. In some examples, the *E. coli* is of the strain BL21 or Rosetta. In still other examples, the *E. coli* is of the strain Origami, provided that the media further comprises sucrose at a concentration of at least 0.4M.

SEQUENCE LISTING

Figure 1:
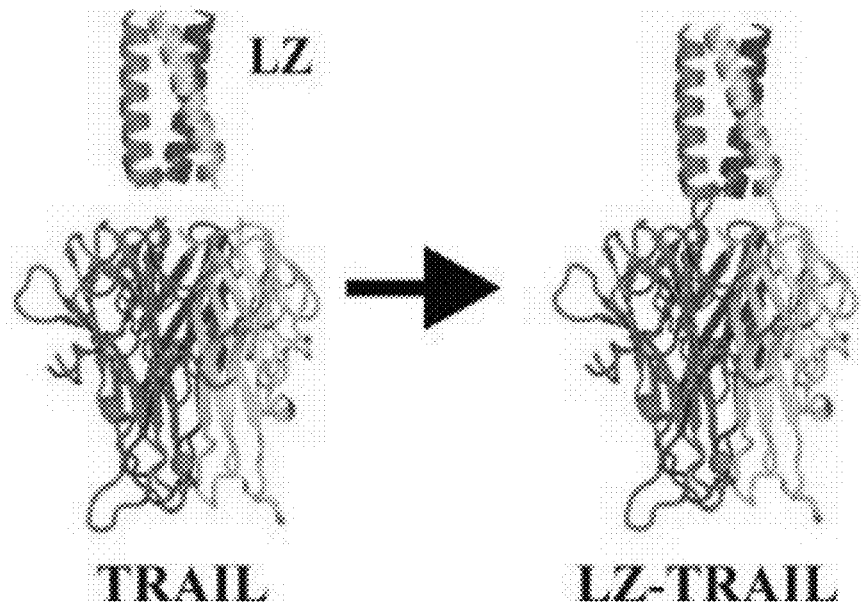
FIG. 1 depicts the general structure of a leucine zipper-TRAIL hybrid.

SEQ ID NO: 1 is a sequence of the leucine zipper motif of human ATF7 with 'a' and 'd' isoleucine substitutions.

SEQ ID NO: 2 is a sequence of the leucine zipper motif of human Matt with 'a' and 'd' isoleucine substitutions.

SEQ ID NO: 3 is a sequence of the leucine zipper motif of human Mat4 with 'a' and 'd' isoleucine substitutions.

SEQ ID NO: 4 is a sequence of the leucine zipper motif of human Cor1A with 'a' and 'd' isoleucine substitutions.

SEQ ID NO: 5 is a sequence of the leucine zipper motif of human DBP with 'a' and 'd' isoleucine substitutions.

SEQ ID NO: 6 is a sequence of the leucine zipper motif of human HLF with 'a' and 'd' isoleucine substitutions.

SEQ ID NO: 7 is a sequence of the leucine zipper motif of human TEF with 'a' and 'd' isoleucine substitutions.

SEQ ID NO: 8 is a sequence of the leucine zipper motif of human C/EBP-β with 'a' and 'd' isoleucine substitutions.

SEQ ID NO: 9 is a sequence of the leucine zipper motif of human TRAF1 with 'a' and 'd' isoleucine substitutions.

SEQ ID NO: 10 is a sequence of the leucine zipper motif of human C/EBP-ε with 'a' and 'd' isoleucine substitutions.

SEQ ID NO: 11 is a sequence of the leucine zipper motif of human C/EBP-γ with 'a' and 'd' isoleucine substitutions.

SEQ ID NO: 12 is a sequence of the leucine zipper motif of human XBP1 with 'a' and 'd' isoleucine substitutions.

SEQ ID NO: 13 is a sequence of the leucine zipper motif of human CREB-H with 'a' and 'd' isoleucine substitutions.

SEQ ID NO: 14 is a sequence of the leucine zipper motif of human CREB4 with 'a' and 'd' isoleucine substitutions.

SEQ ID NO: 15 is a sequence of the leucine zipper motif of human NEMO with 'a' and 'd' isoleucine substitutions.

SEQ ID NO: 16 is a sequence of the leucine zipper motif of human NRP with 'a' and 'd' isoleucine substitutions.

SEQ ID NO: 17 is a sequence of the leucine zipper motif of human β-PIX with 'a' and 'd' isoleucine substitutions.

SEQ ID NO: 18 is a sequence of the leucine zipper motif of human TRAF1 with 'a' and 'd' isoleucine substitutions.

SEQ ID NO: 19 is a sequence of the leucine zipper motif of human NRBI with 'a' and 'd' isoleucine substitutions.

SEQ ID NO: 20 is a sequence of the leucine zipper of ATF7 with a linker.

SEQ ID NO: 21 is a human TRAIL sequence.

SEQ ID NO: 22 is an example sequence of human TRAIL comprising an S133P mutation.

SEQ ID NO: 23 is a mutated version of human TRAIL comprising S156C and L169C mutations.

SEQ ID NO: 24 is a mutated version of human TRAIL comprising T127C and H270C mutations.

SEQ ID NO: 25 is a mutated version of human TRAIL comprising S133P, S156C and L169C mutations.

SEQ ID NO: 26 is a mutated version of human TRAIL comprising S133P, T127C and H270C mutations.

SEQ ID NO: 27 is a mutated version of human TRAIL comprising S156C, L169C, T127C and H270C mutations.

SEQ ID NO: 28 is a mutated version of human TRAIL comprising S133P, S156C, L169C, T127C, and H270C mutations.

SEQ ID NO: 29 is the sequence of the construct described as ATF7-LZ3 herein.

SEQ ID NO: 30 is the sequence of the construct described as ATF7-LZ3 S133P herein.

SEQ ID NO: 31 is the sequence of the construct described as ATF7-LZ3 S156C-L169C herein.

SEQ ID NO: 32 is the sequence of the construct described as ATF7-LZ3 T127C-H270C herein.

SEQ ID NO: 33 is the sequence of the construct described as ATF7-LZ3 S156C-L169C S133P herein.

SEQ ID NO: 34 is the sequence of the construct described as ATF7-LZ3 T127C-H270C S133P herein.

SEQ ID NO: 35 is the sequence of the construct described as ATF7-LZ3 S156C-L169C T127C-H270C herein.

SEQ ID NO: 36 is the sequence of the construct described as ATF7-L23 S156C-L169C T127C-H270C S133P herein.

SEQ ID NO: 37 is a linker.

SEQ ID NO: 38 is a linker.

DETAILED DESCRIPTION

A TRAIL hybrid that is both potent and safe in normal cells is described in the art. This hybrid comprises a yeast GCN4-pII leucine zipper with isoleucine substitutions in the "a" and "d: positions fused to human TRAIL (GCN4-TRAIL) (Rozanov et al, 2009 infra). The insertion of the GCN4-pII leucine zipper motif at the N-terminus of TRAIL stabilizes the formation of the TRAIL trimers due to the ability of the Ile residues in the "a" and "d" positions to drive leucine zipper trimer formation (Harbury P B et al 1993 supra). However, a yeast leucine zipper sequence can be immunogenic in humans.

Disclosed herein are TRAIL hybrids in which the yeast GCN4-pII leucine zipper motif described in the art is replaced with a human leucine zipper peptide to produce a fully human leucine zipper-TRAIL (LZ-TRAIL) chimera. These recombinant polypeptides exhibit a potent antitumor activity in both cell-based tests and at least in one case, in a xenograft model of tumor growth.

The disclosed polypeptides comprise a first sequence that comprises human TRAIL or a homolog thereof. Examples of such sequences that comprise human TRAIL include any sequence comprising SEQ ID NO: 21 herein, any mutant of SEQ ID NO: 21 that results in one or more conservative amino acid substitutions, or any mutant of SEQ ID NO: 21 that functions in the same manner, way, or yields the same result as SEQ ID NO: 21. One of skill in the art in light of this disclosure would be able to generate mutants relative to SEQ ID NO: 21, express them, and test them for expression and function without undue experimentation.

Said homologs can have at least 50%, at least 60%, at least 70%, at least 80%, at least 90%, at least 95%, at least 98%, at least 99% or 100% identity to SEQ ID NO: 21. A conservative amino acid substitution is a substitution of one amino acid to an amino acid that is similar in structure. Examples of conservative substitutions include Ala→Ser; Arg→Lys; Asn→Gln, His; Asp→Glu; Cys→Ser; Gln→Asn; Glu→Asp; His→Asn, Gln; Ile→Leu, Val; Leu→Ile, Val; Lys→Arg, Gln, Glu; Met→Leu,Ile; Phe→Met, Leu, Tyr; Ser→Thr; Thr→Ser; Trp→Tyr; Tyr-→Trp, Phe; Val→Ile, Leu.

The first sequence can also comprise engineered mutations, where such engineered mutations result in polypeptides with desirable characteristics relative to the unmutated human TRAIL. Such desirable characteristics include potency and stability of the expressed polypeptide. Such mutations include amino acid substitution mutations such as S133P, S156C, L169C, T127C, or H270C. These mutations can be engineered in any combination, such as in any combination of one, two, three, four, or five of the mutations. Examples of such mutated forms of the first sequence include SEQ ID NOs: 22-28 herein.

Figure 2:
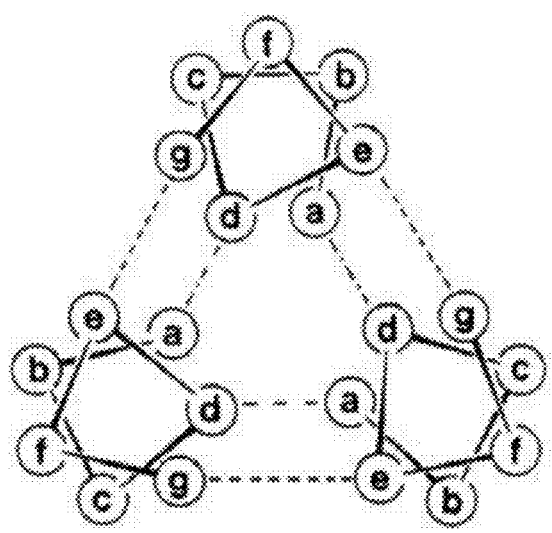
FIG. 2 is a helical wheel diagram of a trimeric leucine zipper coiled-coil. One heptad repeat is shown down the major axes of the helices. Interhelical hydrophobic a/d and electrostatic e/g interactions in the leucine zipper structure are indicated by dashed lines (described in (Harbury P B et al, *Science* 262, 1401-1407 (1993); incorporated by reference herein).

The disclosed polypeptides also comprise a second sequence that is a mutant human leucine zipper motif with one or more isoleucine substitutions incorporated into the 'a' and 'd' positions of the leucine zipper motif as illustrated in FIG. 2 herein and Harbury et al, 1993 supra. Examples of the second sequence include, but are not limited to: SEQ ID NO: 1; SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

The disclosed polypeptides can also comprise a linker between the first sequence and the second sequence. The disclosed polypeptides can also comprise no linker (such as in SEQ ID NOs: 29-35). Examples of linkers include KGSG (SEQ ID NO: 37), GSG, SG, or RGSG (SEQ ID NO: 38).

In still further examples, the disclosed polypeptides comprise the combination of leucine zipper motif and linker of SEQ ID NO: 20.

In further examples, the disclosed polypeptides are encoded by polynucleotides. The polynucleotides can be codon optimized for recombinant expression in *E. coli*, yeast, mammalian cells (such as CHO or other cells) and could comprise any combination of nucleic acid codons that result in the expression of the polypeptide. The polynucleotides can be cloned into any applicable plasmid vector such as an expression vector. The expression vector comprises a promoter that drives transcription of mRNA from the coding sequence for the polypeptide and translation of the mRNA into the protein. The promoter can be any promoter such as constitutively active, inducible, or conditional promoter or a promoter specific for expression in the cell type in which the polypeptides are expressed. The promoter is operably linked to the oligonucleotide. The expression vector can also comprise transcriptional enhancers, silencers, repressors, or any other transcriptional element that can be useful in expression.

In still further examples, an effective amount of the disclosed polypeptides are incorporated into pharmaceutical compositions with pharmaceutically acceptable carriers. These pharmaceutical compositions can be used to treat a subject with cancer.

Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In addition, the materials, methods, and examples are illustrative only and not intended to be limiting. In order to facilitate review of the various embodiments of the disclosure, the following explanations of specific terms are provided:

Administration: To provide or give a subject an agent, such as a recombinant humanized leucine zipper/TRAIL construct, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Cancer: A disease or condition in which abnormal cells divide without control and are able to invade other tissues. Cancer cells spread to other body parts through the blood and lymphatic systems. Cancer is a term for many diseases. There are more than 100 different types of cancer in humans. Most cancers are named after the organ in which they originate. For instance, a cancer that begins in the colon may be called a colon cancer. However, the characteristics of a cancer, especially with regard to the sensitivity of the cancer to therapeutic compounds, are not limited to the organ in which the cancer originates. A cancer cell is any cell derived from any cancer, whether in vitro or in vivo. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" or "metastasis" refers to cancer cells that have left the original tumor site and migrate to other parts of the body for example via the bloodstream or lymph system. The "pathology" of cancer includes all phenomena that compromise the well-being of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

Effective amount: a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

Mutation: A mutation can be any difference in the sequence of a biomolecule relative to a reference or consensus sequence of that biomolecule. A mutation can be observed in a nucleic acid sequence or a protein sequence. Such a reference or consensus sequence may be referred to as "wild type". As disclosed herein, a mutation is purposefully engineered into a polypeptide through recombinant DNA technology. One example of such a mutation is an isoleucine substitution mutation in the "a" and "d' positions of leucine zipper motifs as described herein.

Operably Linked: A first nucleic acid sequence is operably linked with a second nucleic acid sequence when the first nucleic acid sequence is placed in such a way that it has an effect upon the second nucleic acid sequence. For instance, a promoter is operably linked to a coding sequence if the promoter affects the transcription or expression of the coding sequence. Operably linked DNA sequences may be contiguous, or they may operate at a distance.

Pharmaceutical composition: A composition containing one or more of the compounds described herein, or a pharmaceutically acceptable salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

Pharmaceutically acceptable carrier: Any ingredient other than the disclosed compounds, or a pharmaceutically acceptable salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration.

Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

Polynucleotide: a polymer of ribonucleic acid (RNA) or deoxyribonucleic acid (DNA). A nucleic acid is made up of four bases; adenine, cytosine, guanine, and thymine/uracil (uracil is used in RNA). A coding sequence from a nucleic acid is indicative of the sequence of the protein encoded by the nucleic acid.

Polypeptide: Any chain of amino acids, regardless of length or posttranslational modification (such as glycosylation, methylation, ubiquitination, phosphorylation, or the like). Herein as well as in the art, the term 'polypeptide' is used interchangeably with peptide or protein, and is used to refer to a polymer of amino acid residues. The term 'residue' can be used to refer to an amino acid or amino acid mimetic incorporated in a polypeptide by an amide bond or amide bond mimetic. Polypeptide sequences are generally written with the N-terminal amino acid on the left and the C-terminal amino acid to the right of the sequence.

Promoter: A promoter can be any of a number of nucleic acid control sequences that directs transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter may be further modulated by enhancer or repressor elements. Numerous examples of promoters are available and well known to those of skill in the art. A nucleic acid comprising a promoter operably linked to a nucleic acid sequence that codes for a particular polypeptide can be termed an expression vector. An expression vector comprising a constitutively active promoter expresses the protein at effectively all times in the cell. A conditionally active promoter directs expression only under certain conditions. For example, a conditionally active promoter might direct expression only in the presence or absence of a particular compound such as a small molecule, amino acid, nutrient, or other compound while a constitutively active promoter directs expression independently of such conditions. A conditionally active promoter might direct expression in a particular cell or tissue type such as neurons or neural tissue, pancreatic cells such as pancreatic beta cells, fibroblasts, tumors, etc.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide can also refer to a polypeptide that has been made using recombinant nucleic acids, including recombinant nucleic acids transferred to a host organism that is not the natural source of the polypeptide.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage identity or similarity (which takes into account conservative amino acid substitutions); the higher the percentage, the more similar the sequences are. Polypeptides or protein domains thereof that have a significant amount of sequence identity and also function the same or similarly to one another (for example, proteins that serve the same functions in different species or mutant forms of a protein that do not change the function of the protein or the magnitude thereof) can be called "homologs."

Methods of alignment of sequences for comparison are well known in the art. Various programs and alignment algorithms are described in: Smith & Waterman, *Adv App/ Math* 2, 482 (1981); Needleman & Wunsch, *J Mol Biol* 48, 443 (1970); Pearson & Lipman, *Proc Natl Acid Sci USA* 85, 2444 (1988); Higgins & Sharp, *Gene* 73, 237-244 (1988); Higgins & Sharp, *CABIOS* 5, 151-153 (1989); Corpet et al, *Nuc Acids Res* 16, 10881-10890 (1988); Huang et al, *Computer App Biosci* 8, 155-165 (1992); and Pearson et al, *Meth Mol Bio* 24, 307-331 (1994). In addition, Altschul et al, *J Mol Biol* 215, 403-410 (1990), presents a detailed consideration of sequence alignment methods and homology calculations.

The NCBI Basic Local Alignment Search Tool (BLAST) (Altschul et al, (1990) supra) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr database, swissprot database, and patented sequences database. Queries searched with the blastn program are filtered with DUST (Hancock & Armstrong, *Comput Appl Biosci* 10, 67-70 (1994.) Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 50%, 60%, 70%, 80%, 90%, 95%, 98%, or 99% sequence identity to a nucleic acid that encodes a protein.

Subject: An animal such as a mammal, including experimental animals such as rodents and non-human primates, livestock and companion animals, as well as human patients. A subject to be treated according to the methods described herein may be one who has been diagnosed with a cancer. Diagnosis can be performed by any method or technique known in the art. One of skill in the art in light of this disclosure will understand that the subject may have been subjected to standard tests or may have been identified as being at risk due to the presence of one or more risk factors associated with the disease or condition.

Treatment: an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

Pharmaceutical Compositions

The compounds disclosed herein may be included in pharmaceutical compositions (including therapeutic and prophylactic formulations), typically combined together with one or more pharmaceutically acceptable carriers (known equivalently as vehicles) and, optionally, other therapeutic ingredients. Such pharmaceutical compositions can formulated for administration to subjects by a variety of mucosal administration modes, including by oral, rectal, intranasal, intrapulmonary, intravitrial, or transdermal delivery, or by topical delivery to other surfaces including the eye. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other examples, the compound can be administered ex vivo by direct exposure to cells, tissues or organs originating from a subject.

To formulate the pharmaceutical compositions, the compound can be combined with various pharmaceutically acceptable additives. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween®-80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7. The compound can be dispersed in any pharmaceutically acceptable carrier, which can include a hydrophilic compound having a capacity to disperse the compound, and any desired additives. The carrier can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a carrier, for example, polylactic acid, poly(lactic acid-glycolic acid) copolymer, polyhydroxybutyric acid, poly(hydroxybutyric acid glycolic acid) copolymer and mixtures thereof.

Alternatively or additionally, synthetic fatty acid esters such as polyglycerin fatty acid esters, sucrose fatty acid esters and the like can be employed as carriers. Hydrophilic polymers and other vehicles can be used alone or in combination, and enhanced structural integrity can be imparted to the vehicle by partial crystallization, ionic bonding, cross-linking and the like. The carrier can be provided in a variety of forms, including fluid or viscous solutions, gels, pastes, powders, microspheres, and films for direct application to a mucosal surface. The compound can be combined with the carrier according to a variety of methods, and release of the compound can be by diffusion, disintegration of the vehicle, or associated formation of water channels. In some circumstances, the compound is dispersed in microcapsules (microspheres) or nanoparticles prepared from a suitable polymer, for example, 5-isobutyl 2-cyanoacrylate (see, for example, Michael et al., *J Pharmacy Pharmacol* 43, 1-5, (1991), and dispersed in a biocompatible dispersing medium, which yields sustained delivery and biological activity over a protracted time.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acidco-glycolic acid), poly(D-lactic acid-co-glycolic acid), and poly(L-lactic acid-coglycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (betahydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof.

Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728, 721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Treatment

Disclosed herein are methods of treating a subject with cancer through administration of one or more of the disclosed compounds. The compounds can be administered by any appropriate route including orally, parenterally, or topically. The administration of a pharmaceutical composition comprising the disclosed compounds can be for prophylactic or therapeutic purposes. For prophylactic and therapeutic purposes, the treatments can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the treatments for viral infection can be provided as repeated doses within a prolonged prophylaxis or treatment regimen that will yield clinically significant results to alleviate one or more symptoms or detectable conditions associated with a neurodegenerative disorder. An effective amount or concentration of the disclosed compounds can be any amount of a composition that alone, or together with one or more additional therapeutic agents, is sufficient to achieve a desired effect in a subject. The effective amount of the agent will be dependent on several factors, including, but not limited to, the subject being treated and the manner of administration of the therapeutic composition. In one example, a therapeutically effective amount or concentration is one that is sufficient to prevent advancement, delay progression, or to cause regression of a disease, or which is capable of reducing symptoms caused by any disease, including cancer.

In one example, a desired effect is to reduce or inhibit one or more symptoms associated with cancer. The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even at least 100%, as compared to how the sign or symptom would have progressed in the absence of the composition or in comparison to currently available treatments.

The actual effective amount will vary according to factors such as the type of cancer to be protected against/therapeutically treated and the particular status of the subject (for example, the subject's age, size, fitness, extent of symptoms, susceptibility factors, and the like) time and route of administration, other drugs or treatments being administered concurrently, as well as the specific pharmacology of treatments for cancer for eliciting the desired activity or biological response in the subject. Dosage regimens can be adjusted to provide an optimum prophylactic or therapeutic response.

An effective amount is also one in which any toxic or detrimental side effects of the compound and/or other biologically active agent is outweighed in clinical terms by therapeutically beneficial effects. A non-limiting range for a therapeutically effective amount of treatments for viral infection within the methods and formulations of the disclosure is about 0.0001 µg/kg body weight to about 10 mg/kg body weight per dose, such as about 0.0001 µg/kg body weight to about 0.001 µg/kg body weight per dose, about 0.001 µg/kg body weight to about 0.01 µg/kg body weight per dose, about 0.01 µg/kg body weight to about 0.1 µg/kg body weight per dose, about 0.1 µg/kg body weight to about 10 µg/kg body weight per dose, about 1 µg/kg body weight to about 100 µg/kg body weight per dose, about 100 µg/kg body weight to about 500 µg/kg body weight per dose, about 500 µg/kg body weight per dose to about 1000 µg/kg body weight per dose, or about 1.0 mg/kg body weight to about 10 mg/kg body weight per dose.

Determination of effective amount is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art, including xenograft models of cancer. Using such models, only ordinary calculations and adjustments are required to determine an appropriate concentration and dose to administer a therapeutically effective amount of the treatments for viral infection (for example, amounts that are effective to alleviate one or more symptoms of cancer).

The polypeptides disclosed herein can be used in the treatment of cancer. Specific examples of cancer include but need not be limited to: Acute lymphoblastic leukemia; Acute myeloid leukemia; Adrenocortical carcinoma; AIDS-related cancers; AIDS-related lymphoma; Anal cancer; Appendix cancer; Astrocytoma, childhood cerebellar or cerebral; Basal cell carcinoma; Bile duct cancer, extrahepatic; Bladder cancer; Bone cancer, Osteosarcoma/Malignant fibrous histiocytoma; Brainstem glioma; Brain tumor; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer, Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer; Liver Cancer (Primary); Lung Cancer, Non-Small Cell; Lung Cancer, Small Cell; Lymphomas; Lymphoma, AIDS-related; Lymphoma, Burkitt; Lymphoma, cutaneous T Cell; Lymphoma, Hodgkin; Lymphomas, Non-Hodgkin (an old classification of all lymphomas except Hodgkin's); Lymphoma, Primary Central Nervous System; Marcus Whittle, Deadly Disease; Macroglobulinemia, Waldenström; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus=and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sézary syndrome; Skin cancer (nonmelanoma); Skin cancer (melanoma); Skin carcinoma, Merkel cell; Small cell lung cancer; Small intestine cancer; Soft tissue sarcoma; Squamous cell carcinoma—see Skin cancer (nonmelanoma); Squamous neck cancer with occult primary, metastatic; Stomach cancer; Supratentorial primitive neuroectodermal tumor, childhood; T-Cell lymphoma, cutaneous (Mycosis Fungoides and Sézary syndrome); Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenström macroglobulinemia and Wilms tumor (kidney cancer.)

EXAMPLES

The following examples are illustrative of disclosed methods and compounds. In light of this disclosure, those of skill in the art will recognize that variations of these examples and other examples of the disclosed methods and compounds would be possible without undue experimentation.

Example 1—Materials and Methods

Antibodies and reagents: All reagents were from Sigma, unless otherwise indicated. Rabbit anti-mouse/rat Asialo GM1 antibodies were obtained from Cedarline. ATPLite® reagent was obtained from Perkin-Elmer. The expression vector pGAPZα was obtained from Invitrogen.

Cells: Human breast carcinoma MDA-MB-231 and prostate carcinoma PPC-1 cells were obtained from ATCC. Human primary hepatocytes were obtained from Lonza and then cultured in hepatocyte cell growth medium (Lonza). MDA-MB-231 and PPC-1 cells were cultured in Dulbecco's modified Eagle's medium (DMEM) supplemented with 10% FBS (DMEM/FBS) and 10 µg/ml of gentamicin.

Leucine zipper motifs: The selection of human leucine zipper motifs was based on the prediction of the helical content in the peptide sequences and strength of different interactions between parallel two- or three-stranded leucine zippers as predicted by the AGADIR1 and bZIP algorithms, respectively (Lacroix E I et al, *J Mol Biol* 284, 173-191 (1998) and Fong J H et al, *Genome Biol* 5, R11 (2004); both of which are incorporated by reference herein). The selected human leucine zipper motifs were derived from matrilins (Matt and Mat4); coronin 1A (Cor1A); albumin D-box binding protein (DBP), hepatic leukemia factor (HLF); thyrotroph embryonic factor (TEF); CCAAT/enhancer-binding protein beta, epsilon, and gamma (C/EBP-β, C/EBP-ε, and C/EBP-γ, respectively); cyclic AMP-dependent transcription factor 7 (ATF7); X-box binding protein 1 (XBP1); cAMP-response element-binding proteins (CREBH and CREB4), NF-kappa-B essential modulator (NEMO), optineurin (NRP), rho guanine nucleotide exchange factor 7 (β-PIX); TNF receptor-associated factor 1 (TRAF1); and neurabin-I (NRBI). Leucine zipper motifs with the Ile substitutions in the "a" and "d" positions (-pII) are shown below the wild type sequences (Table 1).

Construction of the secretion vector, stability analysis, expression, and purification of TRAIL: The Gln120-Gly281 portion of the human TRAIL gene was linked by PCR via a 2-4 amino acid residues linker or without any linker to the modified human leucine zipper motifs where amino acid residues in the "a" and "d" positions of the peptide sequence were mutated to isoleucine. The leucine zipper-TRAIL fusion constructs were cloned into the pGAPZα plasmid and the resulting expression vectors were transfected into yeast *P. pastoris* cells. At least 50 clones of each construct were evaluated for their ability to induce cytotoxicity in the prostate carcinoma cell line PPC-1. TRAIL construct expressing yeast cells were inoculated into 1 ml of YPD medium and grown overnight at 30° C. The following day, a set number of cells from each clone were diluted into 10 ml of YPD and grown for an additional 24 hours.

At the end of the second growth period, the media was collected for use in cytotoxicity assays. The ratio of dead cells as compared to untreated cells was determined using the ATPLite® reagent. For TRAIL stability testing, conditioned medium from selected *P. pastoris* clones was heated for 20 min at 70° C. and then used in cytotoxicity assays. The change in cytotoxic activity of each clone after the heat treatment was recorded. Expression an purification of leucine zipper-TRAIL fusion proteins was performed as described (Rozanov D V et al, *Mol Cancer Ther* 8, 1515-1525 (2009); incorporated by reference herein).

Cell viability assays: Cells were grown to subconfluency in a 96-well plate and incubated 24 hours with varying concentrations of TRAIL in DMEM/FBS. The extent of cell lysis (percent of dead cells) was determined using ATPLite®.

Caspase Assay: The Caspase-Glo 3/7® luminescent assay (Promega) was used to determine caspase-3/7 activity. The resulting luminescence was measured using a plate reader (Tecan).

Analytical ultracentrifugation and differential scanning calorimetry (DSC): Sedimentation equilibrium experiments were performed using a ProteomeLab XL-I® (Beckman-Coulter) analytical ultracentrifuge. Leucine zipper-TRAIL fusions (0.5, 0.17, and 0.06 mg/ml) in PBS were loaded in the 6-channel equilibrium cells and spun at 20° C. for 24 hours in an An-50 Ti 8-place rotor at 18,000 rpm. Data were analyzed using HeteroAnalysis software. DSC of ATF7-TRAIL (0.5 mg/ml in PBS) was performed at a scanning rate of 1 K/min under 3.0 atm of pressure using an N-DSC II differential scanning calorimeter (calorimetry Sciences).

Tumor xenografts: An orthotropic tumor xenograft assay in immunodeficient mice was used to test the anti-tumor activity of the ATF7-TRAIL chimera in vivo. Two groups of immunocompromised female NOD-SCID mice (7-11 mice/group) were administered an i.v. injection of the asialo-GM-1 antibody (0.1 mg/animal) to inactivate natural killer cells. Immediately after injection of the antibody, MDA-MB-231 cells ($1\times10^6$ in 0.1 ml PBS) were injected into the mammary fat pad. The treatment group received injections of purified ATF7-TRAIL (5 mg/kg) i.p. daily for 10 days. The control group received PBS. On day 4, the i.v. injection of the asialo-GM-lantibody was repeated. Tumor growth was monitored for an additional 7 days after the last ATF7-TRAIL injection. Mice were then sacrificed in accordance with NIH guidelines. Tumors were excised, cleaned from the connective tissue, measured, weighed, and photographed.

Example 2—Design and Selection of the ATF7-TRAIL Chimera

Different human leucine zipper motifs with isoleucine substitutions at the "a" and "d" positions of the leucine zipper sequence were tested for their ability to stabilize the trimeric structure of TRAIL (FIG. 1 and Table 1). It has previously been disclosed that substitution of all residues in the "a" and "d" positions for Ile results in a highly stable GCN4-pII leucine zipper trimeric structure with Tm>100° C. (Harbury P B et al, 1993 supra). The effect of the isoleucine substitutions on the cytotoxic activity of the resulting TRAIL constructs is shown in Table 2.

TABLE 2

Ratio of dead cells after treatment with a TRAIL hybrid with the indicated leucine zipper motif relative to an untreated control. Conditioned media from TRAIL producing P. pastoris clones was diluted 1:100 in DMEM/FBS. Subconfluent prostate carcinoma PPC-1 cells in a 96 well plate were incubated with 1 and 3 µl of the diluted TRAIL samples for 24 hours. At the end of treatment, the ratio of dad cells was determined by an ATPLite reagent. Conditioned medium from non-transfected yeast cells was not cytotoxic to PPC-1 cells.

| Sample volume | Leucine Zipper Motif | | | | | | | | |
|---|---|---|---|---|---|---|---|---|---|
| | CEBP-γ | XBP1 | NRP | NEMO | MAT2 | MAT4 | HLF | DBP | TEF |
| 3 | 53 | 14 | 80 | 24 | 47 | 28 | 68 | 83 | 79 |
| 1 | 24 | 7 | 48 | 18 | 34 | 16 | 28 | 61 | 48 |
| | TRAF1 | PIX | NRB1 | COR1A | CEBP-β | CEBP-ε | ATF7 | CREBH | CREB4 |
| 3 | 3 | 60 | 40 | 15 | 23 | 18 | 85 | 64 | 49 |
| 1 | 0 | 32 | 15 | 7 | 11 | 6 | 65 | 32 | 17 |

After extensive testing, several leucine zipper-TRAIL producing P. pastoris clones were selected for stability analysis (Table 3). The results showed that the ATF7-pII leucine zipper (SEQ ID NO: 1—VSSIEKKIEEITSQIIQIS-NEITLIRNEIAQIKQ) with the isoleucine substitutions at the "a" and "d" positions (underlined in the sequence) was the most efficient in stabilizing the trimeric structure of TRAIL.

TABLE 3

Stability of LZ-TRAIL fusion proteins. The ratio of dead cells was determined as described in the legend for Table 2. Residual cytotoxic activity of the TRAIL samples after 20 minutes at 70° C. was calculated for 3 and 10 µl of 100-fold diluted TRAIL samples.

| Residual Activity | Leucine Zipper Motif | | | | | | | | |
|---|---|---|---|---|---|---|---|---|---|
| | NRP | PIX | HLF | DBP | TEF | NRBI | CREB4 | ATF7 | CREBH |
| 10 | 93 | 85 | 97 | 98 | 96 | 38 | 84 | 100 | 78 |
| 3 | 72 | 53 | 71 | 79 | 84 | 26 | 51 | 93 | 41 |

Example 3—ATF7-TRAIL is a Stable Trimer

Figure 3:
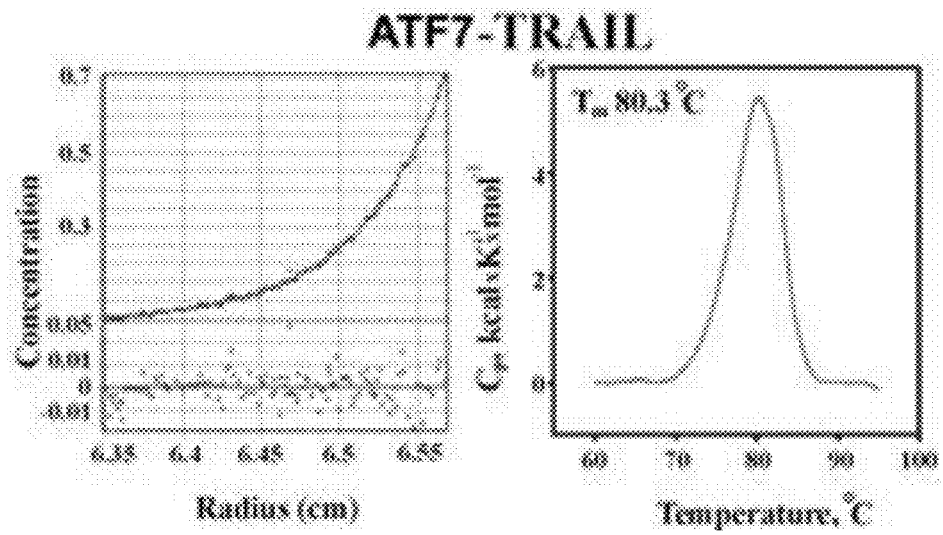
FIG. 3 left panel depicts he sedimentation equilibrium trace of ATF7-TRAIL. The solid line is the best fit achieved using a Monomer-Nmer model. The right panel depicts the melting trace of ATF7-TRAIL. The melting temperature (Tm 80.3° C.) value derived from the scan shows that ATF7-TRAIL was correctly folded and stable.

The fusion of the ATF7 leucine zipper motif to the TRAIL sequence resulted in a highly stable homotrimer. Ultracentrifugation analysis showed that the molecular mass of ATF7-TRAIL is 70.6 kDa (the calculated molecular mass of the ATF7-TRAIL trimer is 69.0 kDa). Sedimentation equilibrium data were analyzed using the Monomer-Nmer model, which showed that ATF7-TRAIL exists solely in its trimeric form (FIG. 3, left panel). The differential scanning calorimetry also indicated that ATF7-TRAIL exists in a single oligomeric form with the melting temperature (Tm) of 80° C. (FIG. 3, right panel). These data suggested that the ATF7-TRAIL fusion protein was properly folded and highly stable.

Figure 4A:
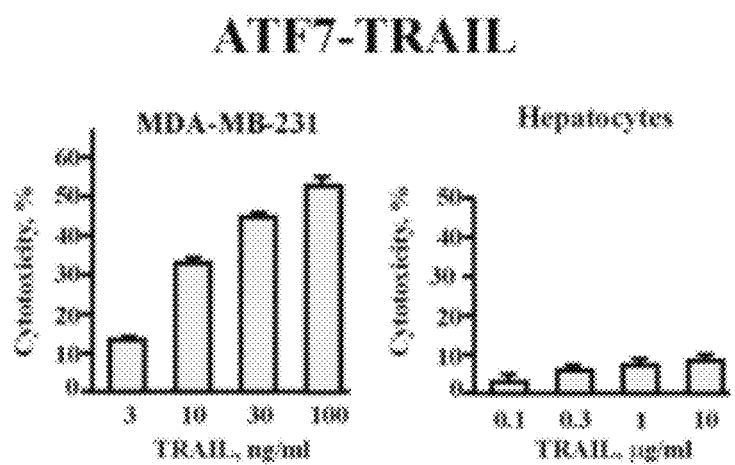
FIG. 4A is a bar graph showing cytotoxicity of ATF7-TRAIL in human breast carcinoma MDA-MB-231 cells and primary hepatocytes at the indicated concentrations. Cytotoxicity was determined by ATP-Lite reagent.

Example 4—Potency and Safety of the Re-Engineered ATF7-TRAIL in Cell-Based Tests ATF7-TRAIL at concentrations as low as 10 ng/ml was highly cytotoxic to MDA-MB-231 breast carcinoma cells (FIG. 4A), despite previous findings suggesting that these cells are considered resistant to TRAIL-mediated apoptosis (Aroui S I, Apoptosis 14, 1352-1365 (2009) and Park C I et al, Acta Pharmacol Sin 29, 341-348 (2008); both of which are incorporated by reference herein. ATF7-TRAIL did not affect the viability of primary human hepatocytes at a concentration as high as 10 µg/ml.

Figure 4B:
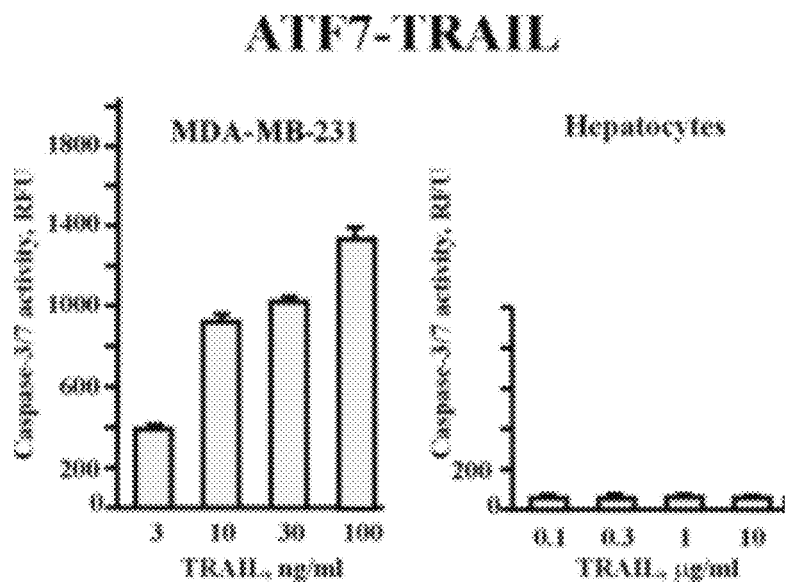
FIG. 4B is a bar graph showing caspase-3/7 activity of ATF7-TRAIL in human breast carcinoma MDA-MB-231 cells and primary hepatocytes at the indicated concentrations. $p<0.05$ at all concentrations.

To further confirm that ATF7-TRAIL induced apoptosis in carcinoma cells but not in normal cells, caspase-3/7 activity was monitored in TRAIL-treated cells. Consistent with the induction of apoptosis, the addition of ATF7-TRAIL resulted in higher caspase-3/7 activity in MDA-MB-231 cells relative to controls. In contrast, caspase-3/7 activity in human hepatocytes treated with ATF7-TRAIL concentrations as high as 10 µg/ml was equivalent to that of controls (FIG. 4B).

Example 5—Anti-Tumor Activity of ATF7-TRAIL In Vivo

Figure 5:
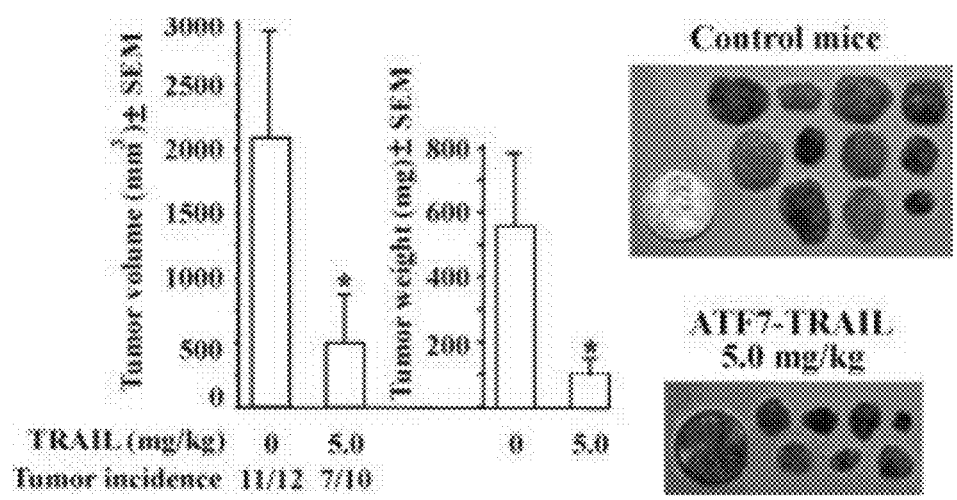
FIG. 5 left panel is a bar graph of the tumor volume and tumor weight of vehicle treated and 5 mg/kg/day ATF7-TRAIL treated mice. Tumor incidence per group is shown below the bars. P=0.004. Right panel shows images of the control and experimental mice.
Figure 6A:
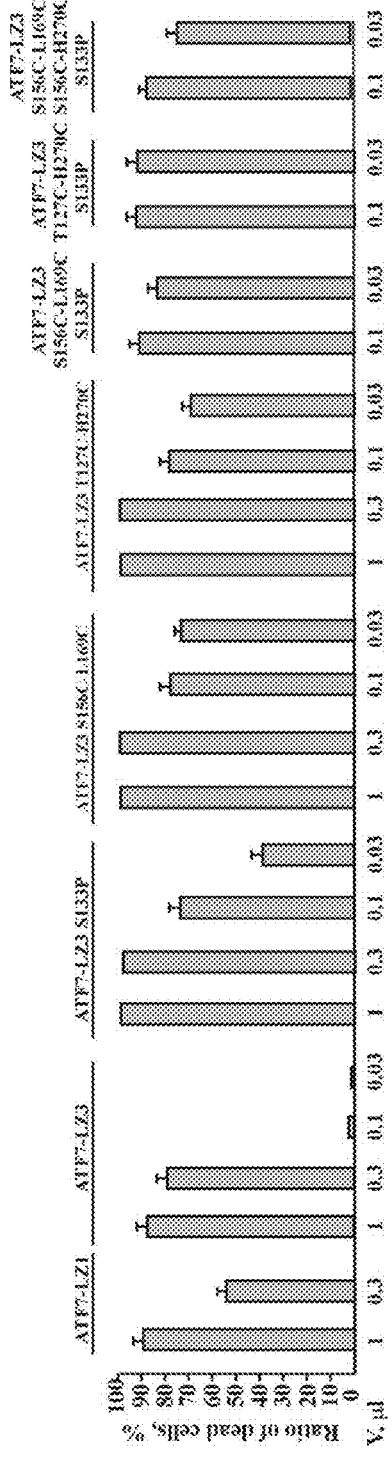
FIG. 6A is a graph showing activity of mutant TRAIL molecules expressed in *Pichia pastoris*. TRAIL-ATF7-113 (ATF7-LZ3) is a derivative of ATF7-LZ1 that lacks the KGSG (SEQ ID NO: 37) linker between the leucine zipper and TRAIL sequence. This linker can create a potential immunogenic site. All mutant TRAIL constructs in the figure are derivatives of ATF7-LZ3. Cells were incubated 24 h at 30° C. followed by centrifugation and collection of conditioned medium. Medium samples were tested in cell viability assays using PPC-1 prostate carcinoma cell as a target. The construct shown in the far right is mislabeled—it should read ATF7-LZ3 S156C-L169C T127C-H270C S133P.
Figure 6B:
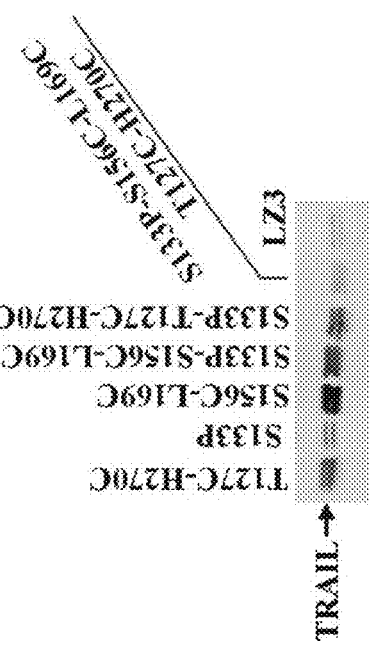
FIG. 6B is an image of a western blot of the conditioned medium collected as described in the description of FIG. 6A above and visualized using Rb-TRAIL antibodies.
Figure 7A:
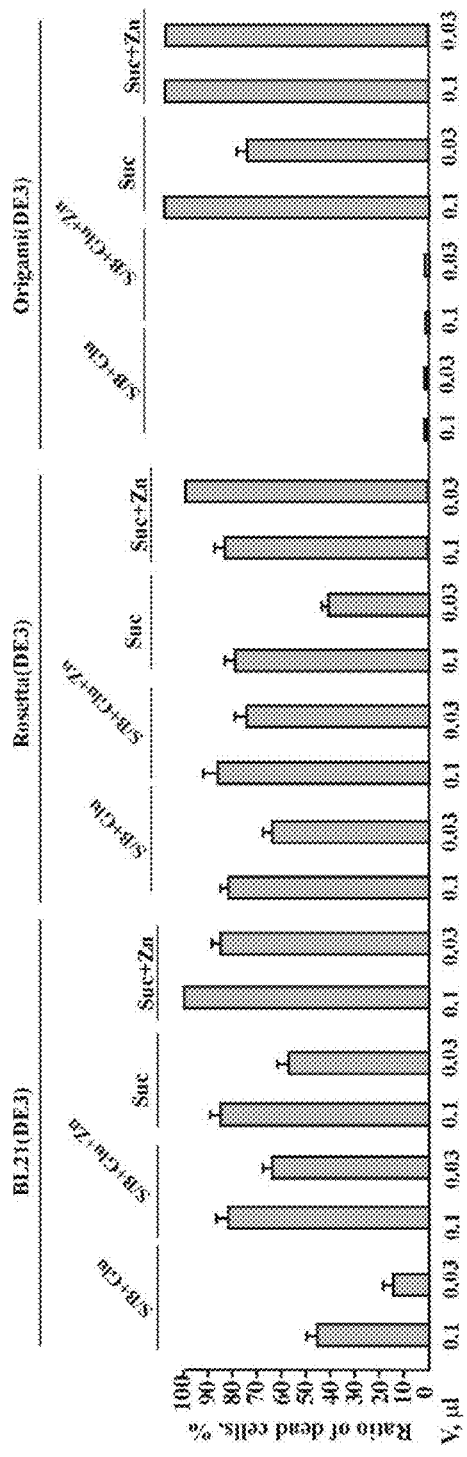
FIG. 7A is a graph showing the results of activity of TRAIL-ATF7-LZ3 expressed in *E. coli*. BL21 (DE3), Rosetta (DE3), and Origami (DE3) cells were transformed with TRAIL-ATF7-LZ3 under different conditions: (1) growth in LB medium containing 50 mM HEPES, pH, 1 mM CaCl2, 1 mM MgCl2, 0.6 M sorbitol, 2.5 mM betaine, and 1% glucose in the presence or absence of 50 μM $ZnCl_2$; (2) growth in LB medium containing 50 mM HEPES, pH, 1 mM $CaCl_2$, 1 mM $MgCl_2$, 7.4, 0.4 M sucrose in the presence or absence of 50 μM $ZnCl_2$. Induction of TRAIL expression was done by 0.3 mM IPTG and cells were grown overnight at 27° C. At the end of induction, cells were collected, disrupted by B-PER 11 reagent and analyzed for both activity cell viability assays using PPC-1 prostate carcinoma cell as a target and presence of TRAIL protein by Western blotting. S/B+Glu, :B medium medium containing 50 mM HEPES, pH, 1 mM CaCl2, 1 mM MgCl2, 0.6 M sorbitol, 2.5 mM betaine, and 1% glucose. S/B+Glu, as for S/B+Glu and also contains 50 μM $ZnCl_2$, Suc, LB medium containing 50 mM HEPES, pH, 1 mM CaCl2, 1 mM MgCl2, 7.4, 0.4 M sucrose; Suc+Zn, as for Suc and also contains 50 μM $ZnCl_2$.
Figure 7B:
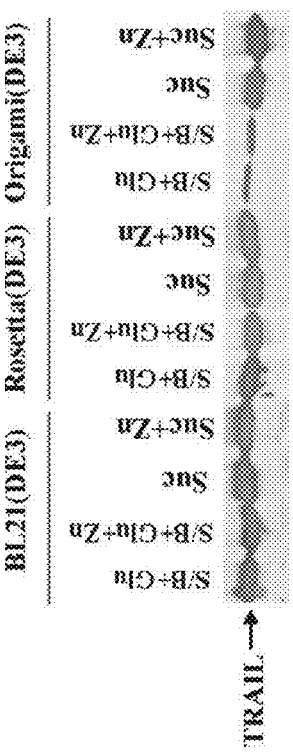
FIG. 7B is an image of a western blot of TRAIL samples collected as described in the description of FIG. 7A and analyzed by Western blotting using Rb-TRAIL antibodies. All abbreviations are as in the description of FIG. 7A.

The ability of ATF7-TRAIL to sensitize MDA-MB-231 cells in vivo was tested using an orthotopic breast cancer xenograft model in mice (FIG. 5). MDA-MB-231 cells were orthotopically xenografted into immunodeficient mice. Animals were randomized into the two groups. The experimental group received an injection of ATF7-TRAIL (5 mg/kg) i.p. daily for 10 days. The control group received PBS alone. We specifically selected a 5 mg/kg dosage of TRAIL because this dosage was used in earlier studies (Rozanov D V et al, 2009 supra). At a 5 mg/kg concentration, ATF7-TRAIL caused a decrease in tumor incidence and a 4-fold reduction in tumor size relative to control, thus confirming the potency of our TRAIL formulation. Administration of ATF7-TRAIL was considered to be safe as no visible signs of gross organ pathology and/or toxicity were found upon post mortem examinations of experimental animals. Moreover, mice did not show any clinical signs of animal distress such as cachexia, cyanosis, dyspnea and ascites, or a lack of mobility and food and water intake at any point during all treatment period.

Example 6—TRAIL Stabilized by Mutations

From Western blotting data it is evident that described mutations affect the yield of TRAIL in *P. pastoris* cells and increased activity of some mutants can result from both increased stability and increased expression of mutant TRAIL. However, expression levels of LZ3, S133P, and S133P-S156C-L169C-T127C-H270C are comparable but their activities are 5-10 times different.

Example 7—TRAIL ATF7-LZ3 Expression in *E. coli*

TRAIL can be expressed in *E. coli* in the trimeric and active form and, with the exception of Origami (DE3)-S/B+Glu, and Origami (DE3)-S/B+Glu+Zn the yield of TRAIL in three strains and under all tested conditions is comparable. However, the highest activity was in TRAIL construct expressed in Origami (DE3) in the presence of 0.4M sucrose and 50 μM $ZnCl_2$. This is important because the Origami strain carries trxB and gor mutations that allow cytoplasmic disulfide bond formation and these cells can be used to express the mutant strains with stabilizing disulfide bonds described herein. Sorbitol and betaine are not compatible with the expression of TRAIL in Origami (DE3) cells. Rosetta cells carry vector with rare codon tRNAs, however, their presence does not increase significantly the level of TRAIL expression.

Example 8—Additional Proposed Work

The described polypeptides can be further tested using humanized mice with an engrafted functional human immune system. Combination with chemotherapeutic agents might further enhance the efficacy of these constructs and overcome tumor resistance to TRAIL therapies (Johnstone R W et al, Nat Rev Cancer 8, 782-798 (2008); Wang S, Oncogene 27, 6207-6215 (2008); and Zhang Y and Zhang B, *Mol Cancer Ther* 6, 1861-1871 (2008); all of which are incorporated by reference herein).

The invention claimed is:

1. A recombinant fusion polypeptide comprising:
   a first sequence comprising an amino acid sequence selected from the group consisting of SEQ ID NO: 21, and SEQ ID NO: 21 with one or more mutations selected from the group consisting of S133P, S156C, L169C, T127C and H270C; and
   a second sequence comprising an amino acid sequence selected from the group consisting of SEQ ID NOs: 1-19.

2. The recombinant fusion polypeptide of claim 1, wherein the recombinant fusion polypeptide further comprises a linker between the first sequence and the second sequence.

3. The recombinant fusion polypeptide of claim 2, wherein the linker is selected from the group consisting of KGSG (SEQ ID NO: 37), GSG, SG, and RGSG (SEQ ID NO: 38).

4. The recombinant fusion polypeptide of claim 3, wherein the recombinant fusion polypeptide comprises the amino acid sequence of SEQ ID NO: 20.

5. The recombinant fusion polypeptide of claim 1, wherein the recombinant fusion polypeptide comprises an amino acid sequence selected from the group consisting of SEQ ID NOs: 22-28.

6. The recombinant fusion polypeptide of claim 5, wherein the recombinant fusion polypeptide lacks a linker between the first sequence and the second sequence.

7. The recombinant fusion polypeptide of claim 6, wherein the recombinant fusion polypeptide comprises an amino acid sequence selected from the group consisting of SEQ ID NOs: 29-36.

8. A pharmaceutical composition comprising an effective amount of the recombinant fusion polypeptide of claim 1 and a pharmaceutically acceptable carrier.

* * * * *

UNITED STATES PATENT AND TRADEMARK OFFICE
CERTIFICATE OF CORRECTION

PATENT NO. : 10,131,701 B2
APPLICATION NO. : 15/081300
DATED : November 20, 2018
INVENTOR(S) : Dmitri Rozanov et al.

It is certified that error appears in the above-identified patent and that said Letters Patent is hereby corrected as shown below:

In the Specification

Column 1, Lines 14-17, within the ACKNOWLEDGEMENT OF GOVERNMENT SUPPORT, please replace:
"This invention was made with the support of the United States government under the terms of grant number W81XWH-09-1-0601, awarded by the Department of Defense."

With:
--This invention was made with government support under W81XWH-09-1-0601 awarded by the U.S. Army Medical Research and Material Command. The government has certain rights in the invention.--.

Signed and Sealed this
Fifth Day of March, 2019

Andrei Iancu
*Director of the United States Patent and Trademark Office*

SEQUENCE LISTING

```
<160> NUMBER OF SEQ ID NOS: 38

<210> SEQ ID NO 1
<211> LENGTH: 34
<212> TYPE: PRT
<213> ORGANISM: Homo sapiens

<400> SEQUENCE: 1

Val Ser Ser Ile Glu Lys Lys Ile Glu Glu Ile Thr Ser Gln Ile Ile
1               5                   10                  15

Gln Ile Ser Asn Glu Ile Thr Leu Ile Arg Asn Glu Ile Ala Gln Ile
            20                  25                  30

Lys Gln

<210> SEQ ID NO 2
<211> LENGTH: 43
<212> TYPE: PRT
<213> ORGANISM: Homo sapiens

<400> SEQUENCE: 2

Glu Lys His Asp Gln Cys Lys Cys Glu Asn Leu Ile Met Phe Gln Asn
1               5                   10                  15

Leu Ala Asn Glu Glu Ile Arg Lys Ile Thr Gln Arg Ile Glu Glu Ile
            20                  25                  30

Thr Gln Arg Ile Glu Ala Ile Glu Asn Arg Leu
        35                  40

<210> SEQ ID NO 3
<211> LENGTH: 42
<212> TYPE: PRT
<213> ORGANISM: Homo sapiens
```

-continued

```
<400> SEQUENCE: 3

Cys Glu Ser Leu Val Glu Phe Gln Gly Arg Ile Leu Gly Ala Ile Glu
1               5                   10                  15

Ser Ile Thr Leu Asn Ile Ala Gln Ile Thr Ala Arg Ile Glu Asp Ile
            20                  25                  30

Glu Asn Gln Cys Glu Ser Leu Val Glu Phe
            35                  40

<210> SEQ ID NO 4
<211> LENGTH: 39
<212> TYPE: PRT
<213> ORGANISM: Homo sapiens

<400> SEQUENCE: 4

Gly Thr Pro Ser Ser Asp Ala Ile Ser Arg Ile Glu Glu Glu Ile Arg
1               5                   10                  15

Lys Ile Gln Ala Thr Ile Gln Glu Ile Gln Gln Arg Ile Asp Arg Ile
            20                  25                  30

Glu Glu Thr Ile Gln Ala Lys
            35

<210> SEQ ID NO 5
<211> LENGTH: 33
<212> TYPE: PRT
<213> ORGANISM: Homo sapiens

<400> SEQUENCE: 5

Glu Lys Glu Ile Ala Leu Ile Arg Gln Glu Ile Val Ala Ile Arg Gln
1               5                   10                  15

Glu Ile Ser His Ile Arg Ala Val Ile Ser Arg Ile Gln Ala Gln His
            20                  25                  30

Gly

<210> SEQ ID NO 6
<211> LENGTH: 33
<212> TYPE: PRT
<213> ORGANISM: Homo sapiens

<400> SEQUENCE: 6

Glu Lys Glu Ile Ser Ala Ile Arg Gln Glu Ile Ala Asp Ile Arg Lys
1               5                   10                  15

Glu Ile Gly Lys Ile Lys Asn Ile Ile Ala Lys Ile Glu Ala Arg His
            20                  25                  30

Gly

<210> SEQ ID NO 7
<211> LENGTH: 31
<212> TYPE: PRT
<213> ORGANISM: Homo sapiens

<400> SEQUENCE: 7

Glu Lys Glu Ile Thr Ala Ile Arg Thr Glu Ile Ala Glu Ile Arg Lys
1               5                   10                  15

Glu Ile Gly Lys Ile Lys Thr Ile Ile Ser Lys Ile Glu Thr Lys
            20                  25                  30

<210> SEQ ID NO 8
<211> LENGTH: 34
<212> TYPE: PRT
```

<400> SEQUENCE: 8

Asn Leu Glu Ile Gln His Lys Ile Leu Glu Ile Thr Ala Glu Ile Glu
1               5                   10                  15

Arg Ile Gln Lys Lys Ile Glu Gln Ile Ser Arg Glu Ile Ser Thr Ile
                20                  25                  30

Arg Asn

<210> SEQ ID NO 9
<211> LENGTH: 47
<212> TYPE: PRT
<213> ORGANISM: Homo sapiens

<400> SEQUENCE: 9

Arg Ala Pro Cys Ser Glu Ser Gln Glu Glu Leu Ala Leu Gln His Phe
1               5                   10                  15

Met Lys Glu Lys Leu Ile Ala Glu Ile Glu Gly Lys Ile Arg Val Ile
                20                  25                  30

Glu Asn Ile Ile Ala Val Ile Asn Lys Glu Ile Glu Ala Ser His
            35                  40                  45

<210> SEQ ID NO 10
<211> LENGTH: 34
<212> TYPE: PRT
<213> ORGANISM: Homo sapiens

<400> SEQUENCE: 10

Ile Leu Glu Ile Gln Gln Lys Ile Leu Glu Ile Met Ala Glu Ile Glu
1               5                   10                  15

Arg Ile Arg Ser Arg Ile Glu Gln Ile Thr Gln Glu Ile Asp Thr Ile
                20                  25                  30

Arg Asn

<210> SEQ ID NO 11
<211> LENGTH: 38
<212> TYPE: PRT
<213> ORGANISM: Homo sapiens

<400> SEQUENCE: 11

Ser Lys Gln Lys Ile Gln Asp Ile Leu Gln Arg Ile Asn Gln Ile Lys
1               5                   10                  15

Glu Glu Ile Glu Arg Ile Glu Ala Lys Ile Lys Leu Ile Thr Lys Glu
                20                  25                  30

Ile Ser Val Ile Lys Asp
            35

<210> SEQ ID NO 12
<211> LENGTH: 42
<212> TYPE: PRT
<213> ORGANISM: Homo sapiens

<400> SEQUENCE: 12

Met Ser Glu Ile Glu Gln Gln Ile Val Asp Ile Glu Glu Glu Ile Gln
1               5                   10                  15

Lys Ile Leu Leu Glu Ile Gln Leu Ile Arg Glu Lys Ile His Gly Ile
                20                  25                  30

Val Val Glu Ile Gln Glu Ile Arg Gln Arg
            35                  40

<210> SEQ ID NO 13
<211> LENGTH: 36
<212> TYPE: PRT
<213> ORGANISM: Homo sapiens

<400> SEQUENCE: 13

Glu Thr Arg Ile Ser Ala Ile Thr Ala Gln Ile Gln Glu Ile Gln Arg
1               5                   10                  15

Lys Ile Leu His Ile Glu Lys Gln Ile Leu Ser Ile Leu Glu Gln Ile
            20                  25                  30

Lys Lys Ile Gln
        35

<210> SEQ ID NO 14
<211> LENGTH: 36
<212> TYPE: PRT
<213> ORGANISM: Homo sapiens

<400> SEQUENCE: 14

Glu Ser Arg Ile Ala Ala Ile Ser Ala Gln Ile Gln Glu Ile Gln Lys
1               5                   10                  15

Lys Ile Gln Glu Ile Glu Arg His Ile Ile Ser Ile Val Ala Gln Ile
            20                  25                  30

Arg Gln Ile Gln
        35

<210> SEQ ID NO 15
<211> LENGTH: 36
<212> TYPE: PRT
<213> ORGANISM: Homo sapiens

<400> SEQUENCE: 15

Gly Met Gln Ile Glu Asp Ile Lys Gln Ile Gln Gln Ile Glu Glu
1               5                   10                  15

Ala Ile Val Ala Ile Gln Glu Val Ile Asp Lys Ile Lys Glu Glu Ile
            20                  25                  30

Glu Gln Ile Lys
        35

<210> SEQ ID NO 16
<211> LENGTH: 39
<212> TYPE: PRT
<213> ORGANISM: Homo sapiens

<400> SEQUENCE: 16

Asp Arg Ala Val Ile Lys Glu Ile Ser Glu Lys Ile Glu Leu Ile Glu
1               5                   10                  15

Lys Ala Ile Ala Ser Ile Gln Leu Gln Ile Asp Glu Ile Lys Gln Thr
            20                  25                  30

Ile Ala Lys Ile Glu Glu Asp
        35

<210> SEQ ID NO 17
<211> LENGTH: 47
<212> TYPE: PRT
<213> ORGANISM: Homo sapiens

<400> SEQUENCE: 17

Glu Glu Lys Ser Leu Val Asp Thr Ile Tyr Ala Ile Lys Asp Glu Ile
1               5                   10                  15

Gln Glu Ile Arg Gln Asp Asn Lys Lys Ile Lys Lys Ser Ile Glu Glu
                20                  25                  30

Ile Gln Arg Ala Ile Lys Asp Leu Glu Lys Leu Ile Arg Lys Ile
                35                  40                  45

<210> SEQ ID NO 18
<211> LENGTH: 52
<212> TYPE: PRT
<213> ORGANISM: Homo sapiens

<400> SEQUENCE: 18

Glu Val Asp Cys Tyr Arg Ala Pro Cys Ser Glu Ser Ile Glu Ile
1               5                   10                  15

Ala Leu Gln Ile Phe Met Ile Glu Lys Leu Ile Ala Glu Ile Glu Gly
                20                  25                  30

Lys Ile Arg Val Ile Glu Asn Ile Ala Val Ile Asn Lys Glu Ile
                35                  40                  45

Glu Ala Ser His
    50

<210> SEQ ID NO 19
<211> LENGTH: 42
<212> TYPE: PRT
<213> ORGANISM: Homo sapiens

<400> SEQUENCE: 19

Ser Pro Ser Glu Leu Asp Ile Ser Lys Ile Ser His Lys Ile Lys Glu
1               5                   10                  15

Ile Gln Ile Lys Ile Ala Val Ile Glu Ala Glu Ile Gln Lys Ile Lys
                20                  25                  30

Thr Lys Ile Gln Ala Ile Glu Asn Glu Lys
                35                  40

<210> SEQ ID NO 20
<211> LENGTH: 38
<212> TYPE: PRT
<213> ORGANISM: Homo sapiens

<400> SEQUENCE: 20

Val Ser Ser Ile Glu Lys Lys Ile Glu Glu Ile Thr Ser Gln Ile Ile
1               5                   10                  15

Gln Ile Ser Asn Glu Ile Thr Leu Ile Arg Asn Glu Ile Ala Gln Ile
                20                  25                  30

Lys Gln Lys Gly Ser Gly
        35

<210> SEQ ID NO 21
<211> LENGTH: 281
<212> TYPE: PRT
<213> ORGANISM: Homo sapiens

<400> SEQUENCE: 21

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
                100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 22
<211> LENGTH: 281
<212> TYPE: PRT
<213> ORGANISM: Homo sapiens

<400> SEQUENCE: 22

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
                100                 105                 110

Leu Val Arg Glu Arg Gly Pro Gln Arg Val Ala Ala His Ile Thr Gly
            115                 120                 125

```
Thr Arg Gly Arg Pro Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
                180                 185                 190

Gln Glu Glu Ile Lys Glu Asn Thr Lys Asn Asp Lys Gln Met Val Gln
                195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270

Ser Phe Phe Gly Ala Phe Leu Val Gly
                275                 280

<210> SEQ ID NO 23
<211> LENGTH: 281
<212> TYPE: PRT
<213> ORGANISM: Homo sapiens

<400> SEQUENCE: 23

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
                35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
                100                 105                 110

Leu Val Arg Glu Arg Gly Pro Gln Arg Val Ala Ala His Ile Thr Gly
                115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Cys Ser Arg Ser Gly
145                 150                 155                 160

His Ser Phe Leu Ser Asn Leu His Cys Arg Asn Gly Glu Leu Val Ile
                165                 170                 175

His Glu Lys Gly Phe Tyr Tyr Ile Tyr Ser Gln Thr Tyr Phe Arg Phe
                180                 185                 190

Gln Glu Glu Ile Lys Glu Asn Thr Lys Asn Asp Lys Gln Met Val Gln
                195                 200                 205

Tyr Ile Tyr Lys Tyr Thr Ser Tyr Pro Asp Pro Ile Leu Leu Met Lys
    210                 215                 220
```

```
Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 24
<211> LENGTH: 281
<212> TYPE: PRT
<213> ORGANISM: Homo sapiens

<400> SEQUENCE: 24

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
            85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Cys Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
            165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp Cys Glu Ala
            260                 265                 270

Ser Phe Phe Gly Ala Phe Leu Val Gly
            275                 280

<210> SEQ ID NO 25
<211> LENGTH: 281
<212> TYPE: PRT
<213> ORGANISM: Homo sapiens
```

<400> SEQUENCE: 25

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Pro Asn Thr Leu Ser Ser Pro Asn Ser Lys Asn Glu
130                 135                 140

Lys Ala Leu Gly Arg Lys Ile Asn Ser Trp Glu Cys Ser Arg Ser Gly
145                 150                 155                 160

His Ser Phe Leu Ser Asn Leu His Cys Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 26
<211> LENGTH: 281
<212> TYPE: PRT
<213> ORGANISM: Homo sapiens

<400> SEQUENCE: 26

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

```
Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Cys Gly
        115                 120                 125

Thr Arg Gly Arg Cys Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp Cys Glu Ala
            260                 265                 270

Ser Phe Phe Gly Ala Phe Leu Val Gly
        275                 280

<210> SEQ ID NO 27
<211> LENGTH: 281
<212> TYPE: PRT
<213> ORGANISM: Homo sapiens

<400> SEQUENCE: 27

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Cys Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Cys Ser Arg Ser Gly
145                 150                 155                 160

His Ser Phe Leu Ser Asn Leu His Cys Arg Asn Gly Glu Leu Val Ile
                165                 170                 175
```

```
His Glu Lys Gly Phe Tyr Tyr Ile Tyr Ser Gln Thr Tyr Phe Arg Phe
                180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp Cys Glu Ala
            260                 265                 270

Ser Phe Phe Gly Ala Phe Leu Val Gly
        275                 280

<210> SEQ ID NO 28
<211> LENGTH: 281
<212> TYPE: PRT
<213> ORGANISM: Homo sapiens

<400> SEQUENCE: 28

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Cys Gly
        115                 120                 125

Thr Arg Gly Arg Pro Asn Thr Leu Ser Ser Pro Asn Ser Lys Asn Glu
130                 135                 140

Lys Ala Leu Gly Arg Lys Ile Asn Ser Trp Glu Cys Ser Arg Ser Gly
145                 150                 155                 160

His Ser Phe Leu Ser Asn Leu His Cys Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255
```

Phe Val Ser Val Thr Asn Glu His Leu Ile Asp Met Asp Cys Glu Ala
            260                 265                 270

Ser Phe Phe Gly Ala Phe Leu Val Gly
        275                 280

<210> SEQ ID NO 29
<211> LENGTH: 315
<212> TYPE: PRT
<213> ORGANISM: Homo sapiens

<400> SEQUENCE: 29

Val Ser Ser Ile Glu Lys Lys Ile Glu Glu Ile Thr Ser Gln Ile Ile
1               5                   10                  15

Gln Ile Ser Asn Glu Ile Thr Leu Ile Arg Asn Glu Ile Ala Gln Ile
            20                  25                  30

Lys Gln Met Ala Met Met Glu Val Gln Gly Gly Pro Ser Leu Gly Gln
        35                  40                  45

Thr Cys Val Leu Ile Val Ile Phe Thr Val Leu Gln Ser Leu Cys
    50                  55                  60

Val Ala Val Thr Tyr Val Tyr Phe Thr Asn Glu Leu Lys Gln Met Gln
65                  70                  75                  80

Asp Lys Tyr Ser Lys Ser Gly Ile Ala Cys Phe Leu Lys Glu Asp Asp
                85                  90                  95

Ser Tyr Trp Asp Pro Asn Asp Glu Glu Ser Met Asn Ser Pro Cys Trp
            100                 105                 110

Gln Val Lys Trp Gln Leu Arg Gln Leu Val Arg Lys Met Ile Leu Arg
        115                 120                 125

Thr Ser Glu Glu Thr Ile Ser Thr Val Gln Glu Lys Gln Gln Asn Ile
    130                 135                 140

Ser Pro Leu Val Arg Glu Arg Gly Pro Gln Arg Val Ala Ala His Ile
145                 150                 155                 160

Thr Gly Thr Arg Gly Arg Ser Asn Thr Leu Ser Ser Pro Asn Ser Lys
                165                 170                 175

Asn Glu Lys Ala Leu Gly Arg Lys Ile Asn Ser Trp Glu Ser Ser Arg
            180                 185                 190

Ser Gly His Ser Phe Leu Ser Asn Leu His Leu Arg Asn Gly Glu Leu
        195                 200                 205

Val Ile His Glu Lys Gly Phe Tyr Tyr Ile Tyr Ser Gln Thr Tyr Phe
    210                 215                 220

Arg Phe Gln Glu Glu Ile Lys Glu Asn Thr Lys Asn Asp Lys Gln Met
225                 230                 235                 240

Val Gln Tyr Ile Tyr Lys Tyr Thr Ser Tyr Pro Asp Pro Ile Leu Leu
                245                 250                 255

Met Lys Ser Ala Arg Asn Ser Cys Trp Ser Lys Asp Ala Glu Tyr Gly
            260                 265                 270

Leu Tyr Ser Ile Tyr Gln Gly Gly Ile Phe Glu Leu Lys Glu Asn Asp
        275                 280                 285

Arg Ile Phe Val Ser Val Thr Asn Glu His Leu Ile Asp Met Asp His
    290                 295                 300

Glu Ala Ser Phe Phe Gly Ala Phe Leu Val Gly
305                 310                 315

<210> SEQ ID NO 30
<211> LENGTH: 315
<212> TYPE: PRT
<213> ORGANISM: Homo sapiens

```
<400> SEQUENCE: 30

Val Ser Ser Ile Glu Lys Lys Ile Glu Glu Ile Thr Ser Gln Ile Ile
 1               5                  10                  15

Gln Ile Ser Asn Glu Ile Thr Leu Ile Arg Asn Glu Ile Ala Gln Ile
             20                  25                  30

Lys Gln Met Ala Met Met Glu Val Gln Gly Gly Pro Ser Leu Gly Gln
             35                  40                  45

Thr Cys Val Leu Ile Val Ile Phe Thr Val Leu Leu Gln Ser Leu Cys
         50                  55                  60

Val Ala Val Thr Tyr Val Tyr Phe Thr Asn Glu Leu Lys Gln Met Gln
65                  70                  75                  80

Asp Lys Tyr Ser Lys Ser Gly Ile Ala Cys Phe Leu Lys Glu Asp Asp
             85                  90                  95

Ser Tyr Trp Asp Pro Asn Asp Glu Glu Ser Met Asn Ser Pro Cys Trp
            100                 105                 110

Gln Val Lys Trp Gln Leu Arg Gln Leu Val Arg Lys Met Ile Leu Arg
            115                 120                 125

Thr Ser Glu Glu Thr Ile Ser Thr Val Gln Glu Lys Gln Gln Asn Ile
        130                 135                 140

Ser Pro Leu Val Arg Glu Arg Gly Pro Gln Arg Val Ala Ala His Ile
145                 150                 155                 160

Thr Gly Thr Arg Gly Arg Pro Asn Thr Leu Ser Ser Pro Asn Ser Lys
                165                 170                 175

Asn Glu Lys Ala Leu Gly Arg Lys Ile Asn Ser Trp Glu Ser Ser Arg
            180                 185                 190

Ser Gly His Ser Phe Leu Ser Asn Leu His Leu Arg Asn Gly Glu Leu
        195                 200                 205

Val Ile His Glu Lys Gly Phe Tyr Tyr Ile Tyr Ser Gln Thr Tyr Phe
    210                 215                 220

Arg Phe Gln Glu Glu Ile Lys Glu Asn Thr Lys Asn Asp Lys Gln Met
225                 230                 235                 240

Val Gln Tyr Ile Tyr Lys Tyr Thr Ser Tyr Pro Asp Pro Ile Leu Leu
                245                 250                 255

Met Lys Ser Ala Arg Asn Ser Cys Trp Ser Lys Asp Ala Glu Tyr Gly
            260                 265                 270

Leu Tyr Ser Ile Tyr Gln Gly Gly Ile Phe Glu Leu Lys Glu Asn Asp
        275                 280                 285

Arg Ile Phe Val Ser Val Thr Asn Glu His Leu Ile Asp Met Asp His
    290                 295                 300

Glu Ala Ser Phe Phe Gly Ala Phe Leu Val Gly
305                 310                 315

<210> SEQ ID NO 31
<211> LENGTH: 315
<212> TYPE: PRT
<213> ORGANISM: Homo sapiens

<400> SEQUENCE: 31

Val Ser Ser Ile Glu Lys Lys Ile Glu Glu Ile Thr Ser Gln Ile Ile
 1               5                  10                  15

Gln Ile Ser Asn Glu Ile Thr Leu Ile Arg Asn Glu Ile Ala Gln Ile
             20                  25                  30

Lys Gln Met Ala Met Met Glu Val Gln Gly Gly Pro Ser Leu Gly Gln
             35                  40                  45
```

-continued

```
Thr Cys Val Leu Ile Val Ile Phe Thr Val Leu Leu Gln Ser Leu Cys
 50                  55                  60

Val Ala Val Thr Tyr Val Tyr Phe Thr Asn Glu Leu Lys Gln Met Gln
 65                  70                  75                  80

Asp Lys Tyr Ser Lys Ser Gly Ile Ala Cys Phe Leu Lys Glu Asp Asp
                 85                  90                  95

Ser Tyr Trp Asp Pro Asn Asp Glu Glu Ser Met Asn Ser Pro Cys Trp
            100                 105                 110

Gln Val Lys Trp Gln Leu Arg Gln Leu Val Arg Lys Met Ile Leu Arg
        115                 120                 125

Thr Ser Glu Glu Thr Ile Ser Thr Val Gln Lys Gln Gln Asn Ile
130                 135                 140

Ser Pro Leu Val Arg Glu Arg Gly Pro Gln Arg Val Ala Ala His Ile
145                 150                 155                 160

Thr Gly Thr Arg Gly Arg Ser Asn Thr Leu Ser Ser Pro Asn Ser Lys
                165                 170                 175

Asn Glu Lys Ala Leu Gly Arg Lys Ile Asn Ser Trp Glu Cys Ser Arg
            180                 185                 190

Ser Gly His Ser Phe Leu Ser Asn Leu His Cys Arg Asn Gly Glu Leu
        195                 200                 205

Val Ile His Glu Lys Gly Phe Tyr Tyr Ile Tyr Ser Gln Thr Tyr Phe
210                 215                 220

Arg Phe Gln Glu Glu Ile Lys Glu Asn Thr Lys Asn Asp Lys Gln Met
225                 230                 235                 240

Val Gln Tyr Ile Tyr Lys Tyr Thr Ser Tyr Pro Asp Pro Ile Leu Leu
                245                 250                 255

Met Lys Ser Ala Arg Asn Ser Cys Trp Ser Lys Asp Ala Glu Tyr Gly
            260                 265                 270

Leu Tyr Ser Ile Tyr Gln Gly Gly Ile Phe Glu Leu Lys Glu Asn Asp
        275                 280                 285

Arg Ile Phe Val Ser Val Thr Asn Glu His Leu Ile Asp Met Asp His
    290                 295                 300

Glu Ala Ser Phe Phe Gly Ala Phe Leu Val Gly
305                 310                 315

<210> SEQ ID NO 32
<211> LENGTH: 315
<212> TYPE: PRT
<213> ORGANISM: Homo sapiens

<400> SEQUENCE: 32

Val Ser Ser Ile Glu Lys Lys Ile Glu Glu Ile Thr Ser Gln Ile Ile
  1               5                  10                  15

Gln Ile Ser Asn Glu Ile Thr Leu Ile Arg Asn Glu Ile Ala Gln Ile
             20                  25                  30

Lys Gln Met Ala Met Met Glu Val Gln Gly Gly Pro Ser Leu Gly Gln
         35                  40                  45

Thr Cys Val Leu Ile Val Ile Phe Thr Val Leu Leu Gln Ser Leu Cys
 50                  55                  60

Val Ala Val Thr Tyr Val Tyr Phe Thr Asn Glu Leu Lys Gln Met Gln
 65                  70                  75                  80

Asp Lys Tyr Ser Lys Ser Gly Ile Ala Cys Phe Leu Lys Glu Asp Asp
                 85                  90                  95

Ser Tyr Trp Asp Pro Asn Asp Glu Glu Ser Met Asn Ser Pro Cys Trp
            100                 105                 110
```

```
Gln Val Lys Trp Gln Leu Arg Gln Leu Val Arg Lys Met Ile Leu Arg
            115                 120                 125

Thr Ser Glu Glu Thr Ile Ser Thr Val Gln Glu Lys Gln Gln Asn Ile
        130                 135                 140

Ser Pro Leu Val Arg Glu Arg Gly Pro Gln Arg Val Ala Ala His Ile
145                 150                 155                 160

Cys Gly Thr Arg Gly Arg Ser Asn Thr Leu Ser Ser Pro Asn Ser Lys
                165                 170                 175

Asn Glu Lys Ala Leu Gly Arg Lys Ile Asn Ser Trp Glu Ser Ser Arg
            180                 185                 190

Ser Gly His Ser Phe Leu Ser Asn Leu His Leu Arg Asn Gly Glu Leu
        195                 200                 205

Val Ile His Glu Lys Gly Phe Tyr Tyr Ile Tyr Ser Gln Thr Tyr Phe
    210                 215                 220

Arg Phe Gln Glu Glu Ile Lys Glu Asn Thr Lys Asn Asp Lys Gln Met
225                 230                 235                 240

Val Gln Tyr Ile Tyr Lys Tyr Thr Ser Tyr Pro Asp Pro Ile Leu Leu
                245                 250                 255

Met Lys Ser Ala Arg Asn Ser Cys Trp Ser Lys Asp Ala Glu Tyr Gly
            260                 265                 270

Leu Tyr Ser Ile Tyr Gln Gly Gly Ile Phe Glu Leu Lys Glu Asn Asp
        275                 280                 285

Arg Ile Phe Val Ser Val Thr Asn Glu His Leu Ile Asp Met Asp Cys
    290                 295                 300

Glu Ala Ser Phe Phe Gly Ala Phe Leu Val Gly
305                 310                 315

<210> SEQ ID NO 33
<211> LENGTH: 315
<212> TYPE: PRT
<213> ORGANISM: Homo sapiens

<400> SEQUENCE: 33

Val Ser Ser Ile Glu Lys Lys Ile Glu Glu Ile Thr Ser Gln Ile Ile
1               5                   10                  15

Gln Ile Ser Asn Glu Ile Thr Leu Ile Arg Asn Glu Ile Ala Gln Ile
            20                  25                  30

Lys Gln Met Ala Met Met Glu Val Gln Gly Gly Pro Ser Leu Gly Gln
        35                  40                  45

Thr Cys Val Leu Ile Val Ile Phe Thr Val Leu Leu Gln Ser Leu Cys
    50                  55                  60

Val Ala Val Thr Tyr Val Tyr Phe Thr Asn Glu Leu Lys Gln Met Gln
65                  70                  75                  80

Asp Lys Tyr Ser Lys Ser Gly Ile Ala Cys Phe Leu Lys Glu Asp Asp
                85                  90                  95

Ser Tyr Trp Asp Pro Asn Asp Glu Glu Ser Met Asn Ser Pro Cys Trp
            100                 105                 110

Gln Val Lys Trp Gln Leu Arg Gln Leu Val Arg Lys Met Ile Leu Arg
        115                 120                 125

Thr Ser Glu Glu Thr Ile Ser Thr Val Gln Glu Lys Gln Gln Asn Ile
    130                 135                 140

Ser Pro Leu Val Arg Glu Arg Gly Pro Gln Arg Val Ala Ala His Ile
145                 150                 155                 160

Thr Gly Thr Arg Gly Arg Pro Asn Thr Leu Ser Ser Pro Asn Ser Lys
                165                 170                 175
```

-continued

Asn Glu Lys Ala Leu Gly Arg Lys Ile Asn Ser Trp Glu Cys Ser Arg
            180                 185                 190

Ser Gly His Ser Phe Leu Ser Asn Leu His Cys Arg Asn Gly Glu Leu
        195                 200                 205

Val Ile His Glu Lys Gly Phe Tyr Tyr Ile Tyr Ser Gln Thr Tyr Phe
    210                 215                 220

Arg Phe Gln Glu Glu Ile Lys Glu Asn Thr Lys Asn Asp Lys Gln Met
225                 230                 235                 240

Val Gln Tyr Ile Tyr Lys Tyr Thr Ser Tyr Pro Asp Pro Ile Leu Leu
                245                 250                 255

Met Lys Ser Ala Arg Asn Ser Cys Trp Ser Lys Asp Ala Glu Tyr Gly
            260                 265                 270

Leu Tyr Ser Ile Tyr Gln Gly Gly Ile Phe Glu Leu Lys Glu Asn Asp
        275                 280                 285

Arg Ile Phe Val Ser Val Thr Asn Glu His Leu Ile Asp Met Asp His
    290                 295                 300

Glu Ala Ser Phe Phe Gly Ala Phe Leu Val Gly
305                 310                 315

<210> SEQ ID NO 34
<211> LENGTH: 315
<212> TYPE: PRT
<213> ORGANISM: Homo sapiens

<400> SEQUENCE: 34

Val Ser Ser Ile Glu Lys Lys Ile Glu Glu Ile Thr Ser Gln Ile Ile
1               5                   10                  15

Gln Ile Ser Asn Glu Ile Thr Leu Ile Arg Asn Glu Ile Ala Gln Ile
            20                  25                  30

Lys Gln Met Ala Met Met Glu Val Gln Gly Gly Pro Ser Leu Gly Gln
        35                  40                  45

Thr Cys Val Leu Ile Val Ile Phe Thr Val Leu Leu Gln Ser Leu Cys
    50                  55                  60

Val Ala Val Thr Tyr Val Tyr Phe Thr Asn Glu Leu Lys Gln Met Gln
65                  70                  75                  80

Asp Lys Tyr Ser Lys Ser Gly Ile Ala Cys Phe Leu Lys Glu Asp Asp
                85                  90                  95

Ser Tyr Trp Asp Pro Asn Asp Glu Glu Ser Met Asn Ser Pro Cys Trp
            100                 105                 110

Gln Val Lys Trp Gln Leu Arg Gln Leu Val Arg Lys Met Ile Leu Arg
        115                 120                 125

Thr Ser Glu Glu Thr Ile Ser Thr Val Gln Glu Lys Gln Gln Asn Ile
    130                 135                 140

Ser Pro Leu Val Arg Glu Arg Gly Pro Gln Arg Val Ala Ala His Ile
145                 150                 155                 160

Cys Gly Thr Arg Gly Arg Cys Asn Thr Leu Ser Ser Pro Asn Ser Lys
                165                 170                 175

Asn Glu Lys Ala Leu Gly Arg Lys Ile Asn Ser Trp Glu Ser Ser Arg
            180                 185                 190

Ser Gly His Ser Phe Leu Ser Asn Leu His Leu Arg Asn Gly Glu Leu
        195                 200                 205

Val Ile His Glu Lys Gly Phe Tyr Tyr Ile Tyr Ser Gln Thr Tyr Phe
    210                 215                 220

Arg Phe Gln Glu Glu Ile Lys Glu Asn Thr Lys Asn Asp Lys Gln Met
225                 230                 235                 240

Val Gln Tyr Ile Tyr Lys Tyr Thr Ser Tyr Pro Asp Pro Ile Leu Leu
            245                 250                 255

Met Lys Ser Ala Arg Asn Ser Cys Trp Ser Lys Asp Ala Glu Tyr Gly
        260                 265                 270

Leu Tyr Ser Ile Tyr Gln Gly Gly Ile Phe Glu Leu Lys Glu Asn Asp
        275                 280                 285

Arg Ile Phe Val Ser Val Thr Asn Glu His Leu Ile Asp Met Asp Cys
    290                 295                 300

Glu Ala Ser Phe Phe Gly Ala Phe Leu Val Gly
305                 310                 315

<210> SEQ ID NO 35
<211> LENGTH: 315
<212> TYPE: PRT
<213> ORGANISM: Homo sapiens

<400> SEQUENCE: 35

Val Ser Ser Ile Glu Lys Lys Ile Glu Glu Ile Thr Ser Gln Ile Ile
1               5                   10                  15

Gln Ile Ser Asn Glu Ile Thr Leu Ile Arg Asn Glu Ile Ala Gln Ile
            20                  25                  30

Lys Gln Met Ala Met Met Glu Val Gln Gly Gly Pro Ser Leu Gly Gln
        35                  40                  45

Thr Cys Val Leu Ile Val Ile Phe Thr Val Leu Leu Gln Ser Leu Cys
    50                  55                  60

Val Ala Val Thr Tyr Val Tyr Phe Thr Asn Glu Leu Lys Gln Met Gln
65                  70                  75                  80

Asp Lys Tyr Ser Lys Ser Gly Ile Ala Cys Phe Leu Lys Glu Asp Asp
                85                  90                  95

Ser Tyr Trp Asp Pro Asn Asp Glu Glu Ser Met Asn Ser Pro Cys Trp
            100                 105                 110

Gln Val Lys Trp Gln Leu Arg Gln Leu Val Arg Lys Met Ile Leu Arg
        115                 120                 125

Thr Ser Glu Glu Thr Ile Ser Thr Val Gln Glu Lys Gln Gln Asn Ile
    130                 135                 140

Ser Pro Leu Val Arg Glu Arg Gly Pro Gln Arg Val Ala Ala His Ile
145                 150                 155                 160

Cys Gly Thr Arg Gly Arg Ser Asn Thr Leu Ser Ser Pro Asn Ser Lys
                165                 170                 175

Asn Glu Lys Ala Leu Gly Arg Lys Ile Asn Ser Trp Glu Cys Ser Arg
            180                 185                 190

Ser Gly His Ser Phe Leu Ser Asn Leu His Cys Arg Asn Gly Glu Leu
        195                 200                 205

Val Ile His Glu Lys Gly Phe Tyr Tyr Ile Tyr Ser Gln Thr Tyr Phe
    210                 215                 220

Arg Phe Gln Glu Glu Ile Lys Glu Asn Thr Lys Asn Asp Lys Gln Met
225                 230                 235                 240

Val Gln Tyr Ile Tyr Lys Tyr Thr Ser Tyr Pro Asp Pro Ile Leu Leu
                245                 250                 255

Met Lys Ser Ala Arg Asn Ser Cys Trp Ser Lys Asp Ala Glu Tyr Gly
            260                 265                 270

Leu Tyr Ser Ile Tyr Gln Gly Gly Ile Phe Glu Leu Lys Glu Asn Asp
        275                 280                 285

Arg Ile Phe Val Ser Val Thr Asn Glu His Leu Ile Asp Met Asp Cys
290                 295                 300

Glu Ala Ser Phe Phe Gly Ala Phe Leu Val Gly
305                 310                 315

<210> SEQ ID NO 36
<211> LENGTH: 315
<212> TYPE: PRT
<213> ORGANISM: Homo sapiens

<400> SEQUENCE: 36

Val Ser Ser Ile Glu Lys Lys Ile Glu Ile Thr Ser Gln Ile Ile
1               5                   10                  15

Gln Ile Ser Asn Glu Ile Thr Leu Ile Arg Asn Glu Ile Ala Gln Ile
                20                  25                  30

Lys Gln Met Ala Met Met Glu Val Gln Gly Gly Pro Ser Leu Gly Gln
                35                  40                  45

Thr Cys Val Leu Ile Val Ile Phe Thr Val Leu Leu Gln Ser Leu Cys
50                  55                  60

Val Ala Val Thr Tyr Val Tyr Phe Thr Asn Glu Leu Lys Gln Met Gln
65                  70                  75                  80

Asp Lys Tyr Ser Lys Ser Gly Ile Ala Cys Phe Leu Lys Glu Asp Asp
                85                  90                  95

Ser Tyr Trp Asp Pro Asn Asp Glu Glu Ser Met Asn Ser Pro Cys Trp
                100                 105                 110

Gln Val Lys Trp Gln Leu Arg Gln Leu Val Arg Lys Met Ile Leu Arg
                115                 120                 125

Thr Ser Glu Glu Thr Ile Ser Thr Val Gln Glu Lys Gln Gln Asn Ile
130                 135                 140

Ser Pro Leu Val Arg Glu Arg Gly Pro Gln Arg Val Ala Ala His Ile
145                 150                 155                 160

Cys Gly Thr Arg Gly Arg Pro Asn Thr Leu Ser Ser Pro Asn Ser Lys
                165                 170                 175

Asn Glu Lys Ala Leu Gly Arg Lys Ile Asn Ser Trp Glu Cys Ser Arg
                180                 185                 190

Ser Gly His Ser Phe Leu Ser Asn Leu His Cys Arg Asn Gly Glu Leu
                195                 200                 205

Val Ile His Glu Lys Gly Phe Tyr Tyr Ile Tyr Ser Gln Thr Tyr Phe
210                 215                 220

Arg Phe Gln Glu Glu Ile Lys Glu Asn Thr Lys Asn Asp Lys Gln Met
225                 230                 235                 240

Val Gln Tyr Ile Tyr Lys Tyr Thr Ser Tyr Pro Asp Pro Ile Leu Leu
                245                 250                 255

Met Lys Ser Ala Arg Asn Ser Cys Trp Ser Lys Asp Ala Glu Tyr Gly
                260                 265                 270

Leu Tyr Ser Ile Tyr Gln Gly Gly Ile Phe Glu Leu Lys Glu Asn Asp
                275                 280                 285

Arg Ile Phe Val Ser Val Thr Asn Glu His Leu Ile Asp Met Asp Cys
290                 295                 300

Glu Ala Ser Phe Phe Gly Ala Phe Leu Val Gly
305                 310                 315

<210> SEQ ID NO 37
<211> LENGTH: 4
<212> TYPE: PRT
<213> ORGANISM: Artificial Sequence

```
<220> FEATURE:
<223> OTHER INFORMATION: linker

<400> SEQUENCE: 37

Lys Gly Ser Gly
1

<210> SEQ ID NO 38
<211> LENGTH: 4
<212> TYPE: PRT
<213> ORGANISM: Artificial sequence
<220> FEATURE:
<223> OTHER INFORMATION: Linker

<400> SEQUENCE: 38

Arg Gly Ser Gly
1
```